US008628753B2

(12) United States Patent
Murthy et al.

(10) Patent No.: US 8,628,753 B2
(45) Date of Patent: Jan. 14, 2014

(54) REDUCED DYE PROBES FOR THE DETECTION OF RADICAL OXYGEN SPECIES

(75) Inventors: Niren Murthy, Atlanta, GA (US); W. Robert Taylor, Stone Mountain, GA (US); Kousik Kundu, Atlanta, GA (US); Sarah F. Knight, Atlanta, GA (US); Sungmun Lee, Dunwoody, GA (US)

(73) Assignees: Emory University, Atlanta, GA (US); Georgia Tech Research Corporation, Atlanta, GA (US)

( * ) Notice: Subject to any disclaimer, the term of this patent is extended or adjusted under 35 U.S.C. 154(b) by 323 days.

(21) Appl. No.: 12/892,379

(22) Filed: Sep. 28, 2010

(65) Prior Publication Data
US 2011/0070166 A1 Mar. 24, 2011

Related U.S. Application Data

(63) Continuation-in-part of application No. PCT/US2009/038772, filed on Mar. 30, 2009.

(60) Provisional application No. 61/040,370, filed on Mar. 28, 2008, provisional application No. 61/100,897, filed on Sep. 29, 2008.

(51) Int. Cl.
*A61B 5/00* (2006.01)
*A61B 8/00* (2006.01)
*A61B 10/00* (2006.01)

(52) U.S. Cl.
USPC ............ 424/9.6; 424/1.11; 424/1.65; 424/9.1

(58) Field of Classification Search
USPC ............ 424/1.11, 1.65, 9.1, 9.2, 9.3, 9.4, 9.5, 424/9.6; 534/550; 540/450; 546/1, 152, 546/184, 249; 548/100, 146, 215, 300.1, 548/400, 950; 549/1, 200; 568/300, 700
See application file for complete search history.

(56) References Cited

U.S. PATENT DOCUMENTS

| 5,321,130 | A | 6/1994 | Yue |
| 5,453,505 | A | 9/1995 | Lee |
| 5,658,751 | A | 8/1997 | Yue |
| 6,159,443 | A * | 12/2000 | Hallahan ...................... 424/1.17 |
| 7,432,372 | B2 | 10/2008 | Batchelor |
| 2005/0214833 | A1 | 9/2005 | Carter |
| 2006/0171893 | A1 | 8/2006 | Zheng |
| 2007/0141658 | A1 | 6/2007 | Chang |

FOREIGN PATENT DOCUMENTS

WO 9600902 1/1996

OTHER PUBLICATIONS

Afri, et al., "Active oxygen chemistry within the liposmal bilayer. Part IV: Locating 2',7'-dichlorofluorescein (DCF), 2',7'-dichlorodihydrofluorescein (DCFH) and 2',7'-dichlorodihydrofluorescein diacetate (DCFH-DA) in the lipid bilayer", Chem. Phys. Lipids, 131:123-33 (2004).
Agarwal and Prabakaran, "Mechanism, measurement, and prevention of oxidative stress in male reproductive physiology", Indian J Exp Bio., 43 (11):963-74 (2005).
Bag and Bag, "Target sequence polymorphism of human manganese superoxide dismutase gene and its association with cancer risk: a review", Cancer Epidemiol Biomarkers Prev., 17(12):3298-3305 (2008).
Blackburn and Taylor, "In situ oxidation-imine formation-reduction routes from alcohols to amines", Org. Lett., 3;1637-39 (2001).
Block, "NADPH oxidase as a therapeutic target in Alzheimer's disease", BMC Neurosci., 9 Suppl. 2:S8, (2008).
Brandes and Schroder, "Differential vascular functions of Nox family NADPH oxidases", Curr Opin Lipidol., 19(5):513-18 (2008).
Cachofeiro, et al. "Oxidative stress and inflammation, a link between chronic kidney disease and cardiovascular disease", Kidney Int. Suppl., 111:S4-9 (2008).
Chen, et al., "Role of increased ROS dissipation in prevention of T1D", Ann. N.Y. Acad. Sci., 1150:157-66 (2008).
Chrissobolis, et al., "The role of oxidative stress and NADPH oxidase in cerebrovascular disease", Trends Mol. Med., 14(11), 495-502 (2008).
Coteur, et al., "Echinoderm reactive oxygen species(ROS) production measured by peroxidase, luminol-enhanced chemiluminescence (PLCL) as an immunotoxicological tool", Prog Mol Subcell Biol., 39:71-83 (2005).
Freinbichler, et al., "The detection of hydroxyl radicals in vivo", J Inor Biochem., 102(5-6)1329-33 (2008).
Gabrielli, et al., "Oxidative stress and the pathogenesis of scleroderma: the Murrell's hypothesis revisited", Semin Immunopathol, 30(3):329-37 (2008).
Gilbert, et al., "Placental ischemia and cardiovascular dysfunction in preeclampsia and beyond: making the connections", Expert. Rev. Cardiovasc. Ther., 6(10), 1367-77 (2008).
Kurien and Scofield, Autoimmunity and oxidatively modified autoantigens, Autoimmun. Rev., 7(7):567-73 (2008).
Lee, "Biomedical application of electron spin resonance (ESR) spectroscopy—assessment of antioxidant property for development of drugs", Yakugaku Zasshi, 128(5):753-63 (2008).
Nistala, et al., "Redox control of renal function and hypertension", Antioxid Redox Signal, 10(12):2047-89 (2008).

(Continued)

*Primary Examiner* — D L Jones
(74) *Attorney, Agent, or Firm* — Pabst Patent Group LLP

(57) ABSTRACT

Reduced dyes, such as hydrocyanines, deuterocyanines, and/or other deuterated dyes capable of detecting one or more reactive oxygen species are described herein. The reduced dyes exhibit little or no fluorescence due to the disrupted π conjugation. However, upon reaction with ROS, the reduced dyes are oxidized, regenerating the extended π conjugation and causing a substantial increase in fluorescence intensity. In many case, the oxidized dye is generally membrane impermeable. However, upon reduction, many of the reduced dyes are membrane permeable. Thus, reduced dyes can accumulate in cells and/or tissue to amplify the signal. Once inside the cell or tissue, the reduced dye is reoxidized upon reaction with ROS, and the oxidized dye again becomes membrane impermeable, trapping the dye within the cell. The reduced dyes can be used to image ROS, such as hydroxide radical and superoxide, in serum, cell cultures, tissue explants, and in vivo.

17 Claims, 4 Drawing Sheets

(56) References Cited

OTHER PUBLICATIONS

Owusu-Ansah, et al., "A protocol for in vivo detection of reactive oxygen species", Nature Protocols, (2008).

Pongnimitprasert, et al., "Potential role of the "NADPH oxidases" (NOX/DUOX) family in cystic fibrosis", Ann. Biol. Clin., 66(6), 621-9 (2008).

Sailer, et al, "Differential effects of deuterium oxide on the fluorescence lifetimes and intensities of dyes with different modes of binding to DNA", J Histochem. Cytochem., 45:165-175 (1997).

Selemidis, et al., "NADPH oxidases in the vasculature: molecular features, roles in disease and pharmacological inhibition", Pharmacol Ther., 120(3):254-91 (2008).

Shea, et al., "Rhodamine dyes as potential agents for photochemotherapy of cancer in human bladder carcinoma cells", Cancer Research, 49:3961-65 (1989).

Stack, et al., "Evidence of oxidant damage in Huntington's disease: translational strategies using antioxidants", Ann. N.Y. Acad. Sci., 1147:79-92 (2008).

Wada, "Sensitive determination of reactive oxygen species by chemiluminescence methods and their application to biological samples and health foods", Yakugaku Zasshi, 128(7):1031-36 (2008).

Wardman, "Fluorescent and luminescent probes for measurement of oxidative and nitrosative species in cells and tissues: progress, pitfalls, and prospects", Free Radic Biol Med., 43(7):995-1022 (2007).

Wozniak and Czyx, "Superoxide dismutase mimetics: possible clinical applications", Postepy Hig Med Dosw, 62:613-24 (2008).

Zhao, et al., "Inflammation and chronic oxidative stress in radiation-induced late normal tissue injury: therapeutic implications", Curr. Med. Chem., 16(2), 130-43 (2009).

Zhou, et al., "Oxidative stress in Parkinson's disease: a mechanism of pathogenic and therapeutic significance", Ann. N.Y. Acad. Sci., 1147:93-104 (2008).

\* cited by examiner

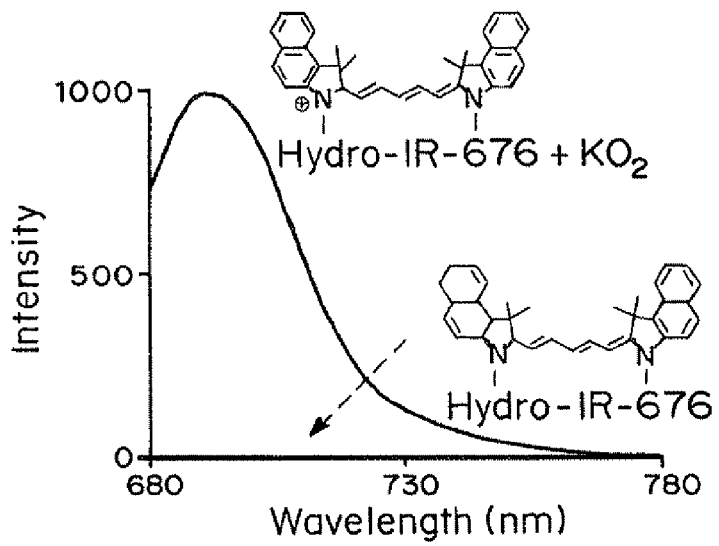
FIG. 1
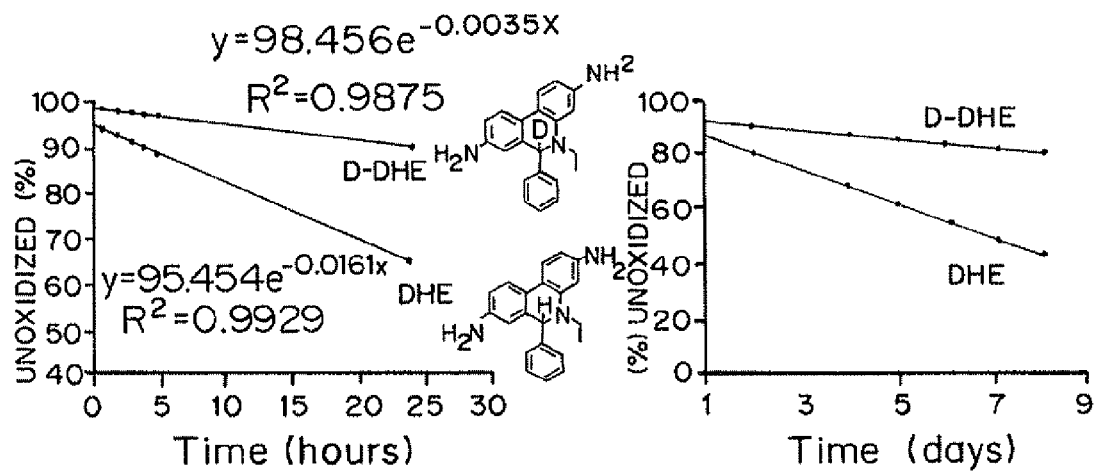
FIG. 2A
FIG. 2B

REDUCED DYE PROBES FOR THE DETECTION OF RADICAL OXYGEN SPECIES

CROSS REFERENCE TO RELATED APPLICATIONS

This application is a continuation-in-part of International Application No. PCT/US2009/038772, filed on Mar. 30, 2009, which claims benefit of and priority to U.S. Provisional Patent Application No. 61/040,370, filed Mar. 28, 2008 and U.S. Provisional Patent Application No. 61/100,897, filed Sep. 29, 2008. These applications are incorporated herein by reference.

STATEMENT REGARDING FEDERALLY SPONSORED RESEARCH OR DEVELOPMENT

The invention was made with Government Support under Agreement No. 5 U01 HL080711-04 awarded by the National Institutes of Health and Grant No. BES-0546962 awarded to by the National Science Foundation. The Government has certain rights in the invention.

FIELD OF THE INVENTION

This invention is generally in the field of probes to detect radical oxygen species in vitro or in vivo, particularly reduced dye probes.

BACKGROUND OF THE INVENTION

The development of fluorescent probes for detection of reactive oxygen species, such as superoxide and/or hydroxyl radicals, is a central problem in the field of chemical biology. Reactive oxygen species, such as superoxide and the hydroxyl radical, play a significant role in a variety of diseases, such as inflammatory diseases, and probes which can detect reactive oxygen species (ROS) in serum samples, live tissue explants, cell cultures, and/or in vivo have tremendous potential as medical diagnostics and research tools for the diagnoses of diseases characterized by increased ROS production.

Fluorescent sensors for superoxide and the hydroxyl radical have been investigated. For example, dihydroethydium (DHE), the structure of which is shown below, has been used as an ROS probe.

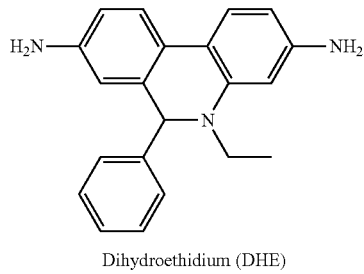 [SMILES: CCN1c2cc(N)ccc2-c2ccc(N)cc2C1c1ccccc1]

Dihydroethidium (DHE)

However, DHE has limited applicability due to its spontaneous auto-oxidation, rapid photobleaching, high toxicity, and multiple reaction products with ROS. Further, the lower emission wavelength of DHE makes it difficult to use in vivo. Dihydrorhodamine, another reduced dye that has been investigated for detection of ROS, also suffers from high rates of aerial oxidation, limiting its applications.

Sulfonate ester-based dyes have also been investigated as ROS probes. However, these probes undergo rapid hydrolysis limiting their applications. Moreover, sulfonate ester-based dyes typically involve multistep synthetic procedures which are time consuming and expensive.

There exists a need for ROS probes that do not suffer from the limitations of prior art probes, such as dihydroethydium, dihydrorhodamine, and sulfonate ester-based dyes.

Therefore, it is an object of the invention to provide improved probes for the detection of ROS, and methods of making and using thereof.

SUMMARY OF THE INVENTION

Reduced dyes including, but not limited to, hydrocyanines, deuterocyanines, and/or other hydro- or deuterated dyes, such as deuterated leuco dyes, capable of detecting one or more reactive oxygen species, are described herein. The reduced dyes are generally prepared by reducing the oxidized dye with a reducing agent, such as sodium borohydride or sodium borodeuteride. For example, hydrocyanines and deuterohydroethydium (D-DHE or DDE) can be synthesized from cyanine dyes via a one-step reduction using a reducing agent, such as sodium borohydride ($NaBH_4$) or sodium borodeuteride ($NaBD_4$). The reduced dyes exhibit little or no fluorescence due to the disrupted π conjugation compared to the oxidized dye. However, upon reaction with ROS, the reduced dyes are oxidized, regenerating the extended π conjugation and causing a substantial increase in fluorescence intensity, compared to the reduced dye, when exposed to radiation of sufficient wavelength. For example, Hydro-IR-676 exhibits negligible fluorescence; however, upon oxidation by ROS (e.g., superoxide), IR-676 exhibits a 100-fold increase in fluorescence emission ($\lambda_{ex}$=675 nm. $\lambda_{em}$=693 nm).

In many cases, the oxidized dye starting material is membrane impermeable. However, upon reduction, many of the reduced dyes are membrane permeable. Thus, reduced dyes can accumulate in cells and/or tissue. Once inside the cell or tissue, the reduced dye is reoxidized upon reaction with ROS, and the oxidized dye again becomes membrane impermeable, trapping the dye within the cell. For example, oxidized cyanine starting materials are generally membrane impermeable. However, upon reduction, many of the hydrocyanines and/or deuterocyanines are membrane permeable. Thus, hydrocyanines and/or reduced cyanines can accumulate in cells and/or tissue.

In one embodiment, the reduced dye is a cyanine dye. Any cyanine dye can be reduced to form a hydrocyanine or deuterocyanine suitable for the compositions and methods of use thereof described herein. In one embodiment, the cyanine dye is fluorescent, but upon reduction, is weakly fluorescent compared to the oxidized dye. In a preferred embodiment, the reduced dye is negligibly fluorescent and membrane permeable, while the oxidized dye is substantially more fluorescent and is membrane impermeable. In another embodiment, the reduced cyanine is negligibly fluorescent, the oxidized cyanine is substantially more fluorescent, and both the reduced cyanine and the oxidized cyanine are membrane impermeable. Upon oxidation by one or more reactive oxygen species, the fluorescence quantum yield increases significantly due to the regeneration of the extended π conjugation.

In another embodiment, the reduced dye is a deuterocyanine or other deuterated dye. A deuterated reduced dye is a dye that has been reduced by a deuterated reducing agent, thereby incorporating deuterium into the reduced cyanine dye. In one embodiment, the deuterated reduced dye is a deuterocyanine. Although the hydrocyanines exhibit excellent stability to auto-oxidation in aqueous solutions, their background oxidation in cell cultures can be improved. The stability of the dyes can be improved by replacing their oxidazable hydrogens with deuterium. Deuterocyanines will likely be more stable to auto-oxidation and exhibit lower levels of background fluorescence in cell cultures than the corresponding hydrocyanines. Oxidation of deuterocyanines generates the identical cyanine dye as their hydrogen analogues, allowing these probes to be used with existing protocols for ROS sensors.

The reduced dyes can be used to image ROS, such as hydroxide radical and superoxide, in vitro, such as in serum, cells, cell cultures, tissue explants, etc., as well as in vivo, such as in cells, tissues, organs, bodily fluids, and combinations thereof. The reduced dyes described herein possess excellent stability to auto-oxidation, have tunable emission wavelengths, and picomolar to millimolar sensitivity. In one embodiment, the reduced dyes have at least nanomolar (e.g., 1-50 nM, preferably 1-30 nM, more preferably 5-30 nM) sensitivity to ROS. The cyanine dyes described herein have emission wavelengths from 500-1100 nm (into the near infrared), which is significantly higher than DHE or sulfonate ester-based dyes, and thus have potential for in vivo applications. This is an important feature since most fluorescent dyes are not effective in vivo since their emission wavelengths are absorbed by surrounding tissue.

BRIEF DESCRIPTION OF THE DRAWINGS

FIG. 1 is a graph showing the fluorescence intensity (RFU/S) of hydro-IR-676 and hydro-IR-676+$KO_2$ (superoxide) as a function of wavelength (nm).

FIG. 2 is a graph comparing the stability to auto-oxidation of DHE (% intact) and D-DHE in solution (FIG. 2a) and as a solid (FIG. 2b) as a function of time (days).

DETAILED DESCRIPTION OF THE INVENTION

I. Definitions

Figure 3A:
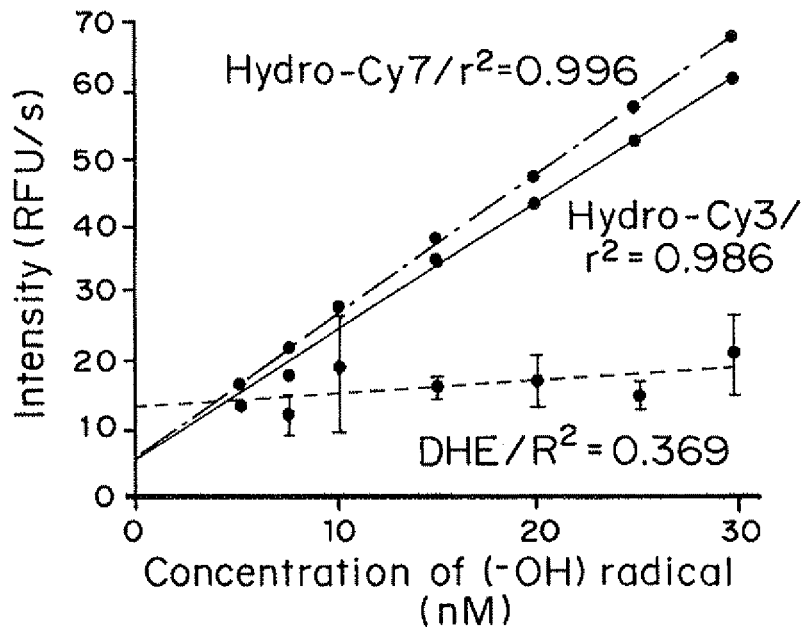
FIG. 3a is a graph comparing the intensity of the fluorescence (relative fluorescence units, RFU/S) of hydro-Cy3, hydro-Cy7, and DHE as a function of hydroxyl radical concentration (nM).

"Reduced dye", as used herein, refers to a dye molecule in which one or more π-bonds have been reduced, disrupting the extended π-conjugation, resulting in a molecule that exhibits negligible or no fluorescence.

"Cyanine dye", as used herein, includes streptocyanines (end groups are open chain or linear moieties), closed chain cyanines (end groups are cyclic moieties), and hemicyanines (one end group is an open chain or linear moiety and the other group is a cyclic moiety). The cyclic moiety can be aromatic or non-aromatic. The linear and/or cyclic moieties can be unsubstituted or substituted at one or more positions. The streptocyanines, closed chain cyanines, and/or hemicyanines can be symmetrical (i.e., end groups are identical) or asymmetrical (i.e., end groups are different).

"Reduced cyanine dye" and "Hydrocyanine" or "Deuterocyanine" are used interchangeably and generally refer to a cyanine dye wherein the iminium cation has been reduced. "Deuterocyanine", as used herein, refers to a cyanine dye that has been reduced by a deuterated reducing agent, thus incorporating deuterium into the reduced molecule. Examples of reduced iminium cations are shown below.

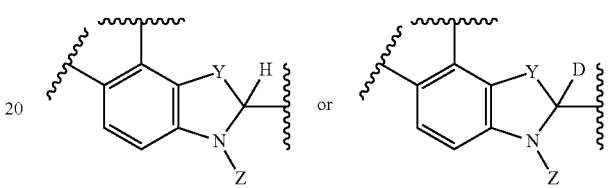

"Reactive oxygen species" and "ROS" are used interchangeably and refer to molecules or ions that contain oxygen ions, free radicals, peroxides, or combinations thereof. Reactive oxygen species can be organic or inorganic. Examples of reactive oxygen species include, but are not limited to, super oxides; free radicals, such as hydroxyl radicals and peroxyl radicals; peroxides, singlet oxygen, ozone, nitrogen monoxide; anions, such as hydroxyl anions and superoxide anions; hypochlorus acid; peroxynitrites; and combinations thereof. In one embodiment, the reduced molecules are selectively sensitive to the presence of hydroxide radical, superoxide, metal-hydrogen peroxide complexes, such as iron-hydrogen peroxide, and combinations thereof.

"Weakly fluorescent" and "negligibly fluorescent" are used interchangeably and generally refers to a fluorescence measurement of less than 10 relative fluorescence units per second (RFU/S).

"Substantially more fluorescent" as used herein, generally means a fluorescence measurement of greater than 10 RFU/S, preferably greater than 20 RFU/S compared to the fluorescence intensity of a reduced dye. In one embodiment, the fluorescence measurement is from about 20 RFU/S to about 1000 RFU/S. In another embodiment, the oxidized dye will increase its fluorescence by at least about 10% compared to the reduced dye after reaction with ROS.

"Membrane permeable" as used herein, refers to a molecule which can enter a cell through passive diffusion. Generally, membrane permeable molecules generally have a Log P of 0.5 or greater (Log P=Log($C_{octane}/C_{water}$).

"Membrane impermeable" as used herein, generally refers to a molecule that cannot diffuse through a cell membrane by passive diffusion either because it is too hydrophilic, too large or bound to an intracellular or extracellular organelle.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amino, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 61'-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., C1-C30 for straight chain, C3-C30 for branched chain), preferably 20 or fewer, more preferably 10 or fewer, most preferably 6 or fewer. If the alkyl is unsaturated, the alkyl chain generally has from 2-30 carbons in the chain, preferably from 2-20 carbons in the chain, more preferably from 2-10 carbons in the chain. Likewise, preferred cycloalkyls have from 3-20 carbon atoms in their ring structure, preferably from 3-10 carbons atoms in their ring structure, most preferably 5, 6 or 7 carbons in the ring structure.

The terms "alkenyl" and "alkynyl" refer to unsaturated aliphatic groups analogous in length and possible substitution to the alkyls described above, but that contain at least one double or triple bond respectively.

The term "alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —$NR_1R_2$, wherein $R_1$ and $R_2$ are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —$CONR_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, —$CF_3$; —CN; —$NCOCOCH_2CH_2$; —NCOCOCHCH; —NCS; and combinations thereof.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

"Alkoxy", "alkylamino", and "alkylthio" are used herein in their conventional sense, and refer to those alkyl groups attached to the remainder of the molecule via an oxygen atom, an amino group, or a sulfur atom, respectively.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $(_{C1-10})$alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents as defined above for alkyl and aryl.

"Halogen", as used herein, refers to fluorine, chlorine, bromine, or iodine.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

The compounds described herein may exist in unsolvated forms as well as solvated forms, including hydrated forms. In general, the solvated forms are equivalent to unsolvated forms and are within the scope of the compounds described herein. The compounds described herein may exist in multiple crystalline or amorphous forms. In general, all physical forms are equivalent for the uses described herein and are intended to be within the scope of the compounds described herein.

The compounds described herein may possess asymmetric carbon atoms (chiral centers) or double bonds; the racemates, diastereomers, geometric isomers and individual isomers are within the scope of the compounds described herein. The compounds described herein may be prepared as a single isomer or as a mixture of isomers. In one, the compounds are prepared as a single isomer, substantially separated from other isomers. Methods of preparing substantially isomerically pure compounds are known in the art.

II. Compounds

Reduced dyes including, but not limited to, hydrocyanines, deuterocyanines, and/or other hydro- or deuterated dyes, such as deuterated leuco dyes, capable of detecting one or more reactive oxygen species, are described herein. The reduced dyes are generally prepared by reducing the oxidized dye with a reducing agent, such as sodium borohydride or sodium borodeuteride. For example, hydrocyanines can be synthesized from cyanine dyes via a one-step reduction using a reducing agent, such as sodium borohydride (NaBH$_4$) or sodium borodeuteride (NaBD$_4$). The reduced dyes exhibit little or no fluorescence, compared to the oxidized dye, due to the disrupted π conjugation. However, upon reaction with ROS, the reduced dyes are oxidized, regenerating the extended π conjugation and causing a substantial increase in fluorescence intensity, compared to the reduced dye, when exposed to radiation of a sufficient wavelength.

For example, Hydro-IR-676 exhibits negligible fluorescence; however, upon oxidation by ROS (e.g., superoxide), IR-676 exhibits a 100-fold increase in fluorescence emission ($\lambda_{ex}$=675 nm. $\lambda_{em}$=693 nm). This is illustrated in FIG. 1.

In the case of the cyanines, the oxidized cyanine starting material is generally membrane impermeable. However, upon reduction, many of the hydrocyanines are membrane permeable. Thus, reduced dyes can accumulate in cells and/or tissue. Once inside the cell or tissue, the reduced dye is reoxidized upon reaction with ROS, and the oxidized dye again becomes membrane impermeable, trapping the dye within the cell. This allows for the accumulation of the probes with cells or tissue, which can serve to amplify the signal.

A. Reduced Cyanine Dyes

Any cyanine dye can be reduced to form a hydrocyanine or deuerocyanine suitable for the compositions and methods of use thereof described herein. The cyanine dye can be an asymmetrical dye or a symmetrical dye. In one embodiment, the cyanine dye is fluorescent, but upon reduction, is weakly fluorescent compared to the oxidized dye. In a preferred embodiment, the reduced dye is negligibly fluorescent, compared to the oxidized dye, and membrane permeable, while the oxidized dye is substantially more fluorescent and is membrane impermeable. In another embodiment, the reduced cyanine is negligibly fluorescent compared to the oxidized dye, the oxidized cyanine is substantially more fluorescent than the reduced dye, and both the reduced cyanine and the oxidized cyanine are membrane impermeable. Upon oxidation by a reactive oxygen species, the fluorescence quantum yield increases dramatically due to the regeneration of the extended π conjugation.

In another embodiment, the reduced dye is a deuterocyanine or other deuterated dye. A deuterated reduced dye is a dye that has been reduced by a deuterated reducing agent, thus incorporating deuterium into the reduced dye. Although the hydrocyanines exhibit excellent stability to auto-oxidation in aqueous solutions, compared to prior art ROS probes such as DHE and sulfonate ester-based dyes, their background oxidation in cell cultures can be improved. The stability of the dyes can be improved by replacing their oxidizable hydrogens with deuterium. Deuterocyanines will likely be more stable to auto-oxidation and exhibit lower levels of background fluoresecence in cell cultures compared to hydrocyanine.

Exemplary reduced dyes include, but are not limited to,

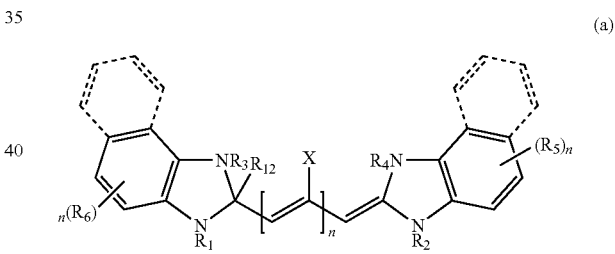

(a)

wherein X is hydrogen; halogen; C$_{1-20}$ alkyl, preferably C$_{1-10}$ alkyl, more preferably C$_{1-6}$ alkyl, most preferably C$_1$, C$_2$ or C$_3$ alkyl; aryl; —OR, where R is C$_{1-20}$ alkyl, preferably C$_{1-10}$ alkyl, more preferably C$_{1-6}$ alkyl, or aryl; hydroxyl; —NR$_5$R$_6$, where R$_5$ and R$_6$ are independently hydrogen, C$_{1-20}$ alkyl, preferably C$_{1-10}$ alkyl, more preferably C$_{1-6}$ alkyl, most preferably C$_1$, C$_2$ or C$_3$ alkyl, or aryl; —CN, —SH; —NO$_2$; —S—C$_{1-20}$ alkyl, preferably C$_{1-10}$ alkyl, more preferably C$_{1-6}$ alkyl, most preferably C$_1$, C$_2$ or C$_3$ alkyl; —S-aryl; aryl, —COOH; —COH; —COR or —COOR, where R is defined above; or —CONR$_{13}$R$_{14}$, wherein R$_{13}$ and R$_{14}$ are independently hydrogen or R as defined above;

R$_1$-R$_4$ are independently hydrogen, C$_{1-20}$ alkyl, preferably C$_{1-10}$ alkyl, more preferably C$_{1-6}$ alkyl, most preferably C$_1$, C$_2$ or C$_3$ alkyl; C$_{1-20}$ alkyl sulfonate, preferably C$_{1-10}$ alkyl sulfonate, more preferably C$_{1-6}$ alkyl sulfonate, most preferably C$_1$, C$_2$, C$_3$, or C$_4$ alkyl sulfonate; C$_{1-20}$ alkyl carboxylic acid or carboxylate, preferably C$_{1-10}$ alkyl carboxylic acid or carboxylate, more preferably C$_{1-6}$ alkyl carboxylic acid or carboxylate, most preferably C$_1$, C$_2$, C$_3$, or C$_4$ alkyl carboxylic acid or carboxylate; C$_{1-20}$ alkyl amino, preferably C$_{1-10}$ alkyl amino or quaternized amino, more preferably C$_{1-6}$ alkyl amino or quaternized amino, most preferably $C_1$, $C_2$, $C_3$, or $C_4$ alkyl amino or quaternized amino; aryl, benzyl, oligoethylene glycol, or polyethylene glycol;

$R_5$ and $R_6$ are independently hydrogen; hydroxyl; —$NH_2$, —$OR_7$; —$NHR_8$; —$NR_9R_{10}$, $C_{1-20}$ alkyl, preferably $C_{1-10}$ alkyl, more preferably $C_{1-6}$ alkyl, most preferably $C_1$, $C_2$ or $C_3$ alkyl; $C_{1-20}$ alkyl sulfonate, preferably $C_{1-10}$ alkyl sulfonate, more preferably $C_{1-6}$ alkyl sulfonate, most preferably $C_1$, $C_2$, $C_3$, or $C_4$ alkyl sulfonate; $C_{1-20}$ alkyl carboxylic acid or carboxylate, preferably $C_{1-10}$ alkyl carboxylic acid or carboxylate, more preferably $C_{1-6}$ alkyl carboxylic acid or carboxylate, most preferably $C_1$, $C_2$, $C_3$, or $C_4$ alkyl carboxylic acid or carboxylate; $C_{1-20}$ alkyl amino or quaternized amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino; —COOH; —$CO_2^-$; or —$SO3^-$; wherein $R_7$-$R_{10}$ are the same as R; oligoethylene glycol, or polyethylene glycol;

n is an integer from 1-5;

$R_{12}$ is H or D; and the benzene ring represented by dotted lines is optional;

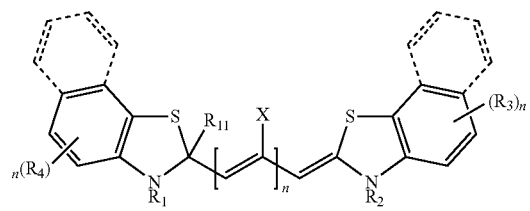

(b)

wherein X is hydrogen; halogen; $C_{1-20}$ alkyl, preferably $C_{1-10}$ alkyl, more preferably $C_{1-6}$ alkyl, most preferably $C_1$, $C_2$ or $C_3$ alkyl; aryl; —OR, where R is $C_{1-20}$ alkyl, preferably $C_{1-10}$ alkyl, more preferably $C_{1-6}$ alkyl, or aryl; hydroxyl; —$NR_5R_6$, where $R_5$ and $R_6$ are independently hydrogen, $C_{1-20}$ alkyl, preferably $C_{1-10}$ alkyl, more preferably $C_{1-6}$ alkyl, most preferably $C_1$, $C_2$ or $C_3$ alkyl, or aryl; —CN, —SH; —$NO_2$; —S—$C_{1-20}$ alkyl, preferably $C_{1-10}$ alkyl, more preferably $C_{1-6}$ alkyl, most preferably $C_1$, $C_2$ or $C_3$ alkyl; —S-aryl; aryl, —COOH; —COH; —COR or —COOR, where R is defined above; or —$CONR_{12}R_{13}$, wherein $R_{12}$ and $R_{13}$ are independently hydrogen or R as defined above;

$R_1$ and $R_2$ are independently hydrogen, $C_{1-20}$ alkyl, preferably $C_{1-10}$ alkyl, more preferably $C_{1-6}$ alkyl, most preferably $C_1$, $C_2$ or $C_3$ alkyl; $C_{1-20}$ alkyl sulfonate, preferably $C_{1-10}$ alkyl sulfonate, more preferably $C_{1-6}$ alkyl sulfonate, most preferably $C_1$, $C_2$, $C_3$, or $C_4$ alkyl sulfate of sulfite; $C_{1-20}$ alkyl carboxylic acid or carboxylate, preferably $C_{1-10}$ alkyl carboxylic acid or carboxylate, more preferably $C_{1-6}$ alkyl carboxylic acid or carboxylate, most preferably $C_1$, $C_2$, $C_3$, or $C_4$ alkyl carboxylic acid or carboxylate; $C_{1-20}$ alkyl amino or quaternized amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino or quaternized amino; aryl, benzyl, oligoethylene glycol, or polyethylene glycol;

$R_3$ and $R_4$ are independently hydrogen; hydroxyl; —$NH_2$, —$OR_9$; —$NHR_{10}$; —$NR_{11}R_{12}$, $C_{1-20}$ alkyl, preferably $C_{1-10}$ alkyl, more preferably $C_{1-6}$ alkyl, most preferably $C_1$, $C_2$ or $C_3$ alkyl; $C_{1-20}$ alkyl sulfonate, preferably $C_{1-10}$ alkyl sulfonate, more preferably $C_{1-6}$ alkyl sulfonate, most preferably $C_1$, $C_2$, $C_3$, or $C_4$ alkyl sulfonate; $C_{1-20}$ alkyl carboxylic acid or carboxylate, preferably $C_{1-10}$ alkyl carboxylic acid or carboxylate, more preferably $C_{1-6}$ alkyl carboxylic acid or carboxylate, most preferably $C_1$, $C_2$, $C_3$, or $C_4$ alkyl carboxylic acid or carboxylate; $C_{1-20}$ alkyl amino or quaternized amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino or quaternized amino; —COOH; —$CO_2^-$; or —$SO_3^-$; wherein $R_9$-$R_{12}$ are the same as R; oligoethylene glycol, or polyethylene glycol;

n is an integer from 1-5;

$R_{11}$ is H or D, and the benzene ring represented by dotted lines is optional.

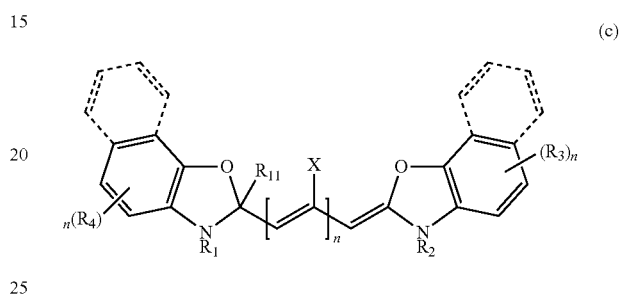

(c)

wherein X is hydrogen; halogen; $C_{1-20}$ alkyl, preferably $C_{1-10}$ alkyl, more preferably $C_{1-6}$ alkyl, most preferably $C_1$, $C_2$ or $C_3$ alkyl; aryl; —OR, where R is $C_{1-20}$ alkyl, preferably $C_{1-10}$ alkyl, more preferably $C_{1-6}$ alkyl, or aryl; hydroxyl; —$NR_5R_6$, where $R_5$ and $R_6$ are independently hydrogen, $C_{1-20}$ alkyl, preferably $C_{1-10}$ alkyl, more preferably $C_{1-6}$ alkyl, most preferably $C_1$, $C_2$ or $C_3$ alkyl, or aryl; —CN, —SH; —$NO_2$; —S—$C_{1-20}$ alkyl, preferably $C_{1-10}$ alkyl, more preferably $C_{1-6}$ alkyl, most preferably $C_1$, $C_2$ or $C_3$ alkyl; —S-aryl; aryl, —COOH; —COH; —COR or —COOR, where R is defined above; or —$CONR_{12}R_{13}$, wherein $R_{12}$ and $R_{13}$ are independently hydrogen or R as defined above;

$R_1$ and $R_2$ are independently hydrogen, $C_{1-20}$ alkyl, preferably $C_{1-10}$ alkyl, more preferably $C_{1-6}$ alkyl, most preferably $C_1$, $C_2$ or $C_3$ alkyl; $C_{1-20}$ alkyl sulfonate, preferably $C_{1-10}$ alkyl sulfonate, more preferably $C_{1-6}$ alkyl sulfonate, most preferably $C_1$, $C_2$, $C_3$, or $C_4$ alkyl sulfonate; $C_{1-20}$ alkyl carboxylic acid or carboxylate, preferably $C_{1-10}$ alkyl carboxylic acid or carboxylate, more preferably $C_{1-6}$ alkyl carboxylic acid or carboxylate, most preferably $C_1$, $C_2$, $C_3$, or $C_4$ alkyl carboxylic acid or carboxylate; $C_{1-20}$ alkyl amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino or quaternized amino; aryl, benzyl, oligoethylene glycol, or polyethylene glycol; and $R_3$ and $R_4$ are independently hydrogen; hydroxyl; —$NH_2$, —$OR_9$; —$NHR_{10}$; —$NR_{11}R_{12}$, $C_{1-20}$ alkyl, preferably $C_{1-10}$ alkyl, more preferably $C_{1-6}$ alkyl, most preferably $C_1$, $C_2$ or $C_3$ alkyl; $C_{1-20}$ alkyl sulfonate, preferably $C_{1-10}$ alkyl sulfonate, more preferably $C_{1-6}$ alkyl sulfonate, most preferably $C_1$, $C_2$, $C_3$, or $C_4$ alkyl sulfonate; $C_{1-20}$ alkyl carboxylic acid or carboxylate, preferably $C_{1-10}$ alkyl carboxylic acid or carboxylate, more preferably $C_{1-6}$ alkyl carboxylic acid or carboxylate, most preferably $C_1$, $C_2$, $C_3$, or $C_4$ alkyl carboxylic acid or carboxylate; $C_{1-20}$ alkyl amino or quaternized amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino or quaternized amino;

—COOH; —CO$_2^-$; or —SO$_3^-$; wherein R$_9$-R$_{12}$ are the same as R; oligoethylene glycol, or polyethylene glycol;

n is an integer from 1-5;

R$_{11}$ is H or D; and the benzene ring represented by dotted lines is optional;

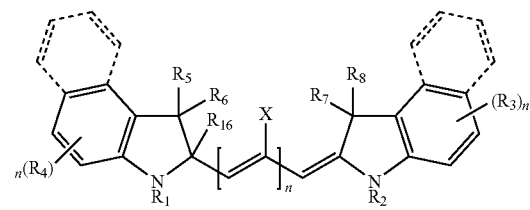

(d)

wherein X is hydrogen; halogen; C$_{1-20}$ alkyl, preferably C$_{1-10}$ alkyl, more preferably C$_{1-6}$ alkyl, most preferably C$_1$, C$_2$ or C$_3$ alkyl; aryl; —OR, where R is C$_{1-20}$ alkyl, preferably C$_{1-10}$ alkyl, more preferably C$_{1-6}$ alkyl, or aryl; hydroxyl; —NR$_5$R$_6$, where R$_5$ and R$_6$ are independently hydrogen, C$_{1-20}$ alkyl, preferably C$_{1-10}$ alkyl, more preferably C$_{1-6}$ alkyl, most preferably C$_1$, C$_2$ or C$_3$ alkyl, or aryl; —CN, —SH; —NO$_2$; —S—C$_{1-20}$ alkyl, preferably C$_{1-10}$ alkyl, more preferably C$_{1-6}$ alkyl, most preferably C$_1$, C$_2$ or C$_3$ alkyl; —S-aryl; aryl, —COOH; —COH; —COR or —COOR, where R is defined above; or —CONR$_{17}$R$_{18}$, wherein R$_{17}$ and R$_{18}$ are independently hydrogen or R as defined above;

R$_1$ and R$_2$ are independently hydrogen, C$_{1-20}$ alkyl, preferably C$_{1-10}$ alkyl, more preferably C$_{1-6}$ alkyl, most preferably C$_1$, C$_2$ or C$_3$ alkyl; C$_{1-20}$ alkyl sulfonate, preferably C$_{1-10}$ alkyl sulfonate, more preferably C$_{1-6}$ alkyl sulfonate, most preferably C$_1$, C$_2$, C$_3$, or C$_4$ alkyl sulfate of sulfite; C$_{1-20}$ alkyl carboxylic acid or carboxylate, preferably C$_{1-10}$ alkyl carboxylic acid or carboxylate, more preferably C$_{1-6}$ alkyl carboxylic acid or carboxylate, most preferably C$_1$, C$_2$, C$_3$, or C$_4$ alkyl carboxylic acid or carboxylate; C$_{1-20}$ alkyl amino, preferably C$_{1-10}$ alkyl amino or quaternized amino, more preferably C$_{1-6}$ alkyl amino or quaternized amino, most preferably C$_1$, C$_2$, C$_3$, or C$_4$ alkyl amino or quaternized amino; aryl, benzyl, oligoethylene glycol, or polyethylene glycol; and R$_3$ and R$_4$ are independently hydrogen; hydroxyl; —NH$_2$, —OR$_9$; —NHR$_{10}$; —NR$_{11}$R$_{12}$, C$_{1-20}$ alkyl, preferably C$_{1-10}$ alkyl, more preferably C$_{1-6}$ alkyl, most preferably C$_1$, C$_2$ or C$_3$ alkyl; C$_{1-20}$ alkyl sulfonate, preferably C$_{1-10}$ alkyl sulfonate, more preferably C$_{1-6}$ alkyl sulfonate, most preferably C$_1$, C$_2$, C$_3$, or C$_4$ alkyl sulfonate; C$_{1-20}$ alkyl carboxylic acid or carboxylate, preferably C$_{1-10}$ alkyl carboxylic acid or carboxylate, more preferably C$_{1-6}$ alkyl carboxylic acid or carboxylate, most preferably C$_1$, C$_2$, C$_3$, or C$_4$ alkyl carboxylic acid or carboxylate; C$_{1-20}$ alkyl amino or quaternized amino, preferably C$_{1-10}$ alkyl amino or quaternized amino, more preferably C$_{1-6}$ alkyl amino or quaternized amino, most preferably C$_1$, C$_2$, C$_3$, or C$_4$ alkyl amino or quaternized amino; —COOH; —CO$_2^-$ or —SO$_3^-$; wherein R$_9$-R$_{12}$ are the same as R; oligoethylene glycol, or polyethylene glycol;

R$_5$-R$_8$ are independently hydrogen or C$_{1-20}$ alkyl, preferably C$_{1-10}$ alkyl, more preferably C$_{1-6}$ alkyl, most preferably C$_1$, C$_2$ or C$_3$ alkyl;

n is an integer from 1-5;

R$_{16}$ is H or D; and the benzene ring represented by dotted lines is optional;

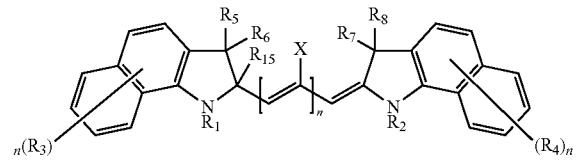

(e)

wherein X is hydrogen; halogen; C$_{1-20}$ alkyl, preferably C$_{1-10}$ alkyl, more preferably C$_{1-6}$ alkyl, most preferably C$_1$, C$_2$ or C$_3$ alkyl; aryl; —OR, where R is C$_{1-20}$ alkyl, preferably C$_{1-10}$ alkyl, more preferably C$_{1-6}$ alkyl, or aryl; hydroxyl; —NR$_5$R$_6$, where R$_5$ and R$_6$ are independently hydrogen, C$_{1-20}$ alkyl, preferably C$_{1-10}$ alkyl, more preferably C$_{1-6}$ alkyl, most preferably C$_1$, C$_2$ or C$_3$ alkyl, or aryl; —CN, —SH; —NO$_2$; —S—C$_{1-20}$ alkyl, preferably C$_{1-10}$ alkyl, more preferably C$_{1-6}$ alkyl, most preferably C$_1$, C$_2$ or C$_3$ alkyl; —S-aryl; aryl, —COOH; —COH; —COR or —COOR, where R is defined above; or —CONR$_{16}$R$_{17}$, wherein R$_{16}$ and R$_{17}$ are independently hydrogen or R as defined above;

R$_1$ and R$_2$ are independently hydrogen, C$_{1-20}$ alkyl, preferably C$_{1-10}$ alkyl, more preferably C$_{1-6}$ alkyl, most preferably C$_1$, C$_2$ or C$_3$ alkyl; C$_{1-20}$ alkyl sulfonate, preferably C$_{1-10}$ alkyl sulfonate, more preferably C$_{1-6}$ alkyl sulfonate, most preferably C$_1$, C$_2$, C$_3$, or C$_4$ alkyl sulfonate; C$_{1-20}$ alkyl carboxylic acid or carboxylate, preferably C$_{1-10}$ alkyl carboxylic acid or carboxylate, more preferably C$_{1-6}$ alkyl carboxylic acid or carboxylate, most preferably C$_1$, C$_2$, C$_3$, or C$_4$ alkyl carboxylic acid or carboxylate; C$_{1-20}$ alkyl amino or quaternized amino, preferably C$_{1-10}$ alkyl amino or quaternized amino, more preferably C$_{1-6}$ alkyl amino or quaternized amino, most preferably C$_1$, C$_2$, C$_3$, or C$_4$ alkyl amino or quaternized amino; aryl, benzyl, oligoethylene glycol, or polyethylene glycol;

R$_3$ and R$_4$ are independently hydrogen; hydroxyl; —NH$_2$, —OR$_9$; —NHR$_{10}$; —NR$_{11}$R$_{12}$, C$_{1-20}$ alkyl, preferably C$_{1-10}$ alkyl, more preferably C$_{1-6}$ alkyl, most preferably C$_1$, C$_2$ or C$_3$ alkyl; C$_{1-20}$ alkyl sulfonate, preferably C$_{1-10}$ alkyl sulfonate, more preferably C$_{1-6}$ alkyl sulfonate, most preferably C$_1$, C$_2$, C$_3$, or C$_4$ alkyl sulfonate; C$_{1-20}$ alkyl carboxylic acid or carboxylate, preferably C$_{1-10}$ alkyl carboxylic acid or carboxylate, more preferably C$_{1-6}$ alkyl carboxylic acid or carboxylate, most preferably C$_1$, C$_2$, C$_3$, or C$_4$ alkyl carboxylic acid or carboxylate; C$_{1-20}$ alkyl amino or quaternized amino, preferably C$_{1-10}$ alkyl amino or quaternized amino, more preferably C$_{1-6}$ alkyl amino or quaternized amino, most preferably C$_1$, C$_2$, C$_3$, or C$_4$ alkyl amino or quaternized amino; —COOH; —CO$_2^-$; or —SO$_3^-$; wherein R$_9$-R$_{12}$ are the same as R; oligoethylene glycol, or polyethylene glycol;

R$_5$-R$_8$ are independently hydrogen or C$_{1-20}$ alkyl, preferably C$_{1-10}$ alkyl, more preferably C$_{1-6}$ alkyl, most preferably C$_1$, C$_2$ or C$_3$ alkyl;

R$_{15}$ is H or D; and n is an integer from 1-5;

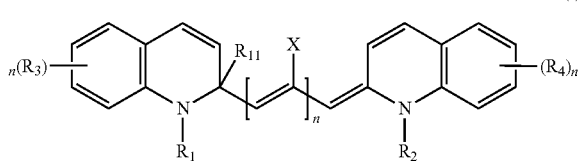

(f)

wherein X is hydrogen; halogen; $C_{1-20}$ alkyl, preferably $C_{1-10}$ alkyl, more preferably $C_{1-6}$ alkyl, most preferably $C_1$, $C_2$ or $C_3$ alkyl; aryl; —OR, where R is $C_{1-20}$ alkyl, preferably $C_{1-10}$ alkyl, more preferably $C_{1-6}$ alkyl, or aryl; hydroxyl; —$NR_5R_6$, where $R_5$ and $R_6$ are independently hydrogen, $C_{1-20}$ alkyl, preferably $C_{1-10}$ alkyl, more preferably $C_{1-6}$ alkyl, most preferably $C_1$, $C_2$ or $C_3$ alkyl, or aryl; —CN, —SH; —$NO_2$; —S—$C_{1-20}$ alkyl, preferably $C_{1-10}$ alkyl, more preferably $C_{1-6}$ alkyl, most preferably $C_1$, $C_2$ or $C_3$ alkyl; —S-aryl; aryl, —COOH; —COH; —COR or —COOR, where R is defined above; or —$CONR_{12}R_{13}$, wherein $R_{12}$ and $R_{13}$ are independently hydrogen or R as defined above;

$R_1$ and $R_2$ are independently hydrogen, $C_{1-20}$ alkyl, preferably $C_{1-10}$ alkyl, more preferably $C_{1-6}$ alkyl, most preferably $C_1$, $C_2$ or $C_3$ alkyl; $C_{1-20}$ alkyl sulfonate, preferably $C_{1-10}$ alkyl sulfonate, more preferably $C_{1-6}$ alkyl sulfonate, most preferably $C_1$, $C_2$, $C_3$, or $C_4$ alkyl sulfate of sulfite; $C_{1-20}$ alkyl carboxylic acid or carboxylate, preferably $C_{1-10}$ alkyl carboxylic acid or carboxylate, more preferably $C_{1-6}$ alkyl carboxylic acid or carboxylate, most preferably $C_1$, $C_2$, $C_3$, or $C_4$ alkyl carboxylic acid or carboxylate; $C_{1-20}$ alkyl amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino or quaternized amino; aryl, benzyl, oligoethylene glycol, or polyethylene glycol; and $R_3$ and $R_4$ are independently hydrogen; hydroxyl; —$OR_5$; —$NH_2$; —$NHR_6$; —$NR_7R_8$, $C_{1-20}$ alkyl, preferably $C_{1-10}$ alkyl, more preferably $C_{1-6}$ alkyl, most preferably $C_1$, $C_2$ or $C_3$ alkyl; $C_{1-20}$ alkyl sulfonate, preferably $C_{1-10}$ alkyl sulfonate, more preferably $C_{1-6}$ alkyl sulfonate, most preferably $C_1$, $C_2$, $C_3$, or $C_4$ alkyl sulfonate; $C_{1-20}$ alkyl carboxylic acid or carboxylate, preferably $C_{1-10}$ alkyl carboxylic acid or carboxylate, more preferably $C_{1-6}$ alkyl carboxylic acid or carboxylate, most preferably $C_1$, $C_2$, $C_3$, or $C_4$ alkyl carboxylic acid or carboxylate; $C_{1-20}$ alkyl amino or quaternized amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino or quaternized amino; —COOH; —$CO_2^-$; or —$SO_3^-$; wherein $R_5$-$R_8$ are the same as R; oligoethylene glycol, or polyethylene glycol;

$R_{11}$ is H or D; and n is an integer from 1-5.

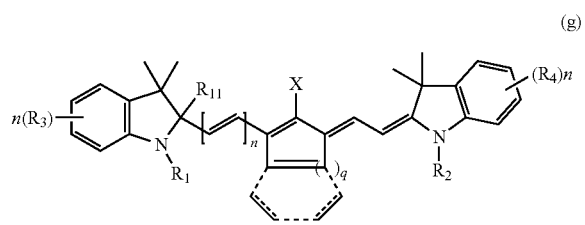

(g)

wherein X is hydrogen; halogen; $C_{1-20}$ alkyl, preferably $C_{1-10}$ alkyl, more preferably $C_{1-6}$ alkyl, most preferably $C_1$, $C_2$ or $C_3$ alkyl; aryl; —OR, where R is $C_{1-20}$ alkyl, preferably $C_{1-10}$ alkyl, more preferably $C_{1-6}$ alkyl, or aryl; hydroxyl; —$NR_5R_6$, where $R_5$ and $R_6$ are independently hydrogen, $C_{1-20}$ alkyl, preferably $C_{1-10}$ alkyl, more preferably $C_{1-6}$ alkyl, most preferably $C_1$, $C_2$ or $C_3$ alkyl, or aryl; —CN, —SH; —$NO_2$; —S—$C_{1-20}$ alkyl, preferably $C_{1-10}$ alkyl, more preferably $C_{1-6}$ alkyl, most preferably $C_1$, $C_2$ or $C_3$ alkyl; —S-aryl; aryl, —COOH; —COH; —COR or —COOR, where R is defined above; or —$CONR_{12}R_{13}$, wherein $R_{12}$ and $R_{13}$ are independently hydrogen or R as defined above;

$R_1$ and $R_2$ are independently hydrogen, $C_{1-20}$ alkyl, preferably $C_{1-10}$ alkyl, more preferably $C_{1-6}$ alkyl, most preferably $C_1$, $C_2$ or $C_3$ alkyl; $C_{1-20}$ alkyl sulfonate, preferably $C_{1-10}$ alkyl sulfonate, more preferably $C_{1-6}$ alkyl sulfonate, most preferably $C_1$, $C_2$, $C_3$, or $C_4$ alkyl sulfonate; $C_{1-20}$ alkyl carboxylic acid or carboxylate, preferably $C_{1-10}$ alkyl carboxylic acid or carboxylate, more preferably $C_{1-6}$ alkyl carboxylic acid or carboxylate, most preferably $C_1$, $C_2$, $C_3$, or $C_4$ alkyl carboxylic acid or carboxylate; $C_{1-20}$ alkyl amino or quaternized amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino or quaternized amino; aryl, benzyl, oligoethylene glycol, or polyethylene glycol; and $R_3$ and $R_4$ are independently hydrogen; hydroxyl; —$OR_5$; —$NH_2$; —$NHR_6$; —$NR_7R_8$, $C_{1-20}$ alkyl, preferably $C_{1-10}$ alkyl, more preferably $C_{1-6}$ alkyl, most preferably $C_1$, $C_2$ or $C_3$ alkyl; $C_{1-20}$ alkyl sulfonate, preferably $C_{1-10}$ alkyl sulfonate, more preferably $C_{1-6}$ alkyl sulfonate, most preferably $C_1$, $C_2$, $C_3$, or $C_4$ alkyl sulfonate; $C_{1-20}$ alkyl carboxylic acid or carboxylate, preferably $C_{1-10}$ alkyl carboxylic acid or carboxylate, more preferably $C_{1-6}$ alkyl carboxylic acid or carboxylate, most preferably $C_1$, $C_2$, $C_3$, or $C_4$ alkyl carboxylic acid or carboxylate; $C_{1-20}$ alkyl amino or quaternized amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino or quaternized amino; —COOH; —$CO_2^-$, or —$SO_3^-$; wherein $R_5$-$R_8$ are the same as R; oligoethylene glycol, or polyethylene glycol;

$R_{11}$ is H or D;

q is 0, 1, or 2;

n is an integer from 1-5; and the benzene ring represented by dotted lines is optional;

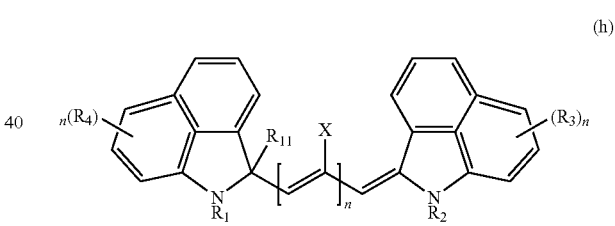

(h)

nized amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino or quaternized amino; aryl, benzyl, oligoethylene glycol, or polyethylene glycol; and $R_3$ and $R_4$ are independently hydrogen; hydroxyl; —$OR_5$; —$NH_2$; —$NHR_6$; —$NR_7R_8$, $C_{1-20}$ alkyl, preferably $C_{1-10}$ alkyl, more preferably $C_{1-6}$ alkyl, most preferably $C_1$, $C_2$ or $C_3$ alkyl; $C_{1-20}$ alkyl sulfonate, preferably $C_{1-10}$ alkyl sulfonate, more preferably $C_{1-6}$ alkyl sulfonate, most preferably $C_1$, $C_2$, $C_3$, or $C_4$ alkyl sulfonate; $C_{1-20}$ alkyl carboxylic acid or carboxylate, preferably $C_{1-10}$ alkyl carboxylic acid or carboxylate, more preferably $C_{1-6}$ alkyl carboxylic acid or carboxylate, most preferably $C_1$, $C_2$, $C_3$, or $C_4$ alkyl carboxylic acid or carboxylate; $C_{1-20}$ alkyl amino or quaternized amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino or quaternized amino; —COOH; —$CO_2^-$; or —$SO_3^-$; wherein $R_5$-$R_8$ are the same as R;

$R_{11}$ is H or D; and n is an integer from 1-5.

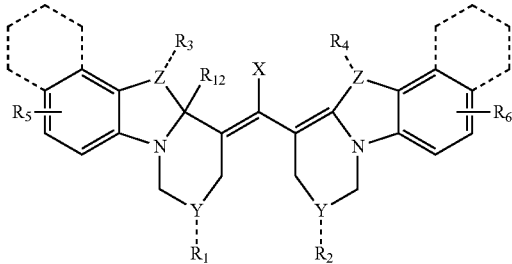

(i)

wherein X is hydrogen; halogen; $C_{1-20}$ alkyl, preferably $C_{1-10}$ alkyl, more preferably $C_{1-6}$ alkyl, most preferably $C_1$, $C_2$ or $C_3$ alkyl; aryl; —OR, where R is $C_{1-20}$ alkyl, preferably $C_{1-10}$ alkyl, more preferably $C_{1-6}$ alkyl, or aryl; hydroxyl; —$NR_5R_6$, where $R_5$ and $R_6$ are independently hydrogen, $C_{1-20}$ alkyl, preferably $C_{1-10}$ alkyl, more preferably $C_{1-6}$ alkyl, most preferably $C_1$, $C_2$ or $C_3$ alkyl, or aryl; —CN, —SH; —$NO_2$; —S—$C_{1-20}$ alkyl, preferably $C_{1-10}$ alkyl, more preferably $C_{1-6}$ alkyl, most preferably $C_1$, $C_2$ or $C_3$ alkyl; —S-aryl; aryl, —COOH; —COH; —COR or —COOR, where R is defined above; or —$CONR_{13}R_{14}$, wherein $R_{13}$ and $R_{14}$ are independently hydrogen or R as defined above;

$R_1$-$R_4$ are independently hydrogen, $C_{1-20}$ alkyl, preferably $C_{1-10}$ alkyl, more preferably $C_{1-6}$ alkyl, most preferably $C_1$, $C_2$ or $C_3$ alkyl; $C_{1-20}$ alkyl sulfonate, preferably $C_{1-10}$ alkyl sulfonate, more preferably $C_{1-6}$ alkyl sulfonate, most preferably $C_1$, $C_2$, $C_3$, or $C_4$ alkyl sulfonate; $C_{1-20}$ alkyl carboxylic acid or carboxylate, preferably $C_{1-10}$ alkyl carboxylic acid or carboxylate, more preferably $C_{1-6}$ alkyl carboxylic acid or carboxylate, most preferably $C_1$, $C_2$, $C_3$, or $C_4$ alkyl carboxylic acid or carboxylate; $C_{1-20}$ alkyl amino or quaternized amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino or quaternized amino; aryl, benzyl, oligoethylene glycol, or polyethylene glycol;

$R_5$ and $R_6$ are independently hydrogen; hydroxyl; —$OR_5$; —$NH_2$; —$NHR_6$; —$NR_7R_8$, $C_{1-20}$ alkyl, preferably $C_{1-10}$ alkyl, more preferably $C_{1-6}$ alkyl, most preferably $C_1$, $C_2$ or $C_3$ alkyl; $C_{1-20}$ alkyl sulfonate, preferably $C_{1-10}$ alkyl sulfonate, more preferably $C_{1-6}$ alkyl sulfonate, most preferably $C_1$, $C_2$, $C_3$, or $C_4$ alkyl sulfonate; $C_{1-20}$ alkyl carboxylic acid or carboxylate, preferably $C_{1-10}$ alkyl carboxylic acid or carboxylate, more preferably $C_{1-6}$ alkyl carboxylic acid or carboxylate, most preferably $C_1$, $C_2$, $C_3$, or $C_4$ alkyl carboxylic acid or carboxylate; $C_{1-20}$ alkyl amino or quaternized amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino or quaternized amino; —COOH; —$CO_2^-$; or —$SO_3^-$; wherein $R_5$-$R_8$ are the same as R; oligoethylene glycol, or polyethylene glycol;

Y and Z are independently carbon, nitrogen or sulfur, wherein if Y and/or Z is carbon, the carbon will be tetravalent having two substituents as defined above; if Y and/or Z is sulfur; the sulfur will be divalent; and if Y and/or Z is nitrogen, the nitrogen will be trivalent, having one substituent as defined above;

$R_{12}$ is H or D; and the benzene ring represented by dotted lines is optional;

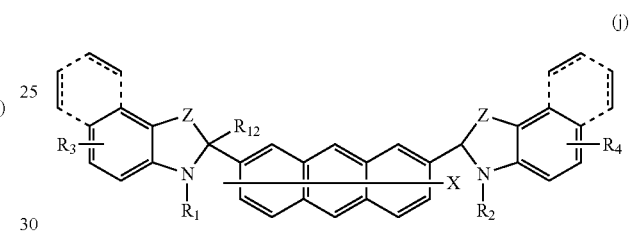

(j)

wherein X is hydrogen; halogen; $C_{1-20}$ alkyl, preferably $C_{1-10}$ alkyl, more preferably $C_{1-6}$ alkyl, most preferably $C_1$, $C_2$ or $C_3$ alkyl; aryl; —OR, where R is $C_{1-20}$ alkyl, preferably $C_{1-10}$ alkyl, more preferably $C_{1-6}$ alkyl, or aryl; hydroxyl; —$NR_5R_6$, where $R_5$ and $R_6$ are independently hydrogen, $C_{1-20}$ alkyl, preferably $C_{1-10}$ alkyl, more preferably $C_{1-6}$ alkyl, most preferably $C_1$, $C_2$ or $C_3$ alkyl, or aryl; —CN, —SH; —$NO_2$; —S—$C_{1-20}$ alkyl, preferably $C_{1-10}$ alkyl, more preferably $C_{1-6}$ alkyl, most preferably $C_1$, $C_2$ or $C_3$ alkyl; —S-aryl; aryl, —COOH; —COH; —COR or —COOR, where R is defined above; or —$CONR_{13}R_{14}$, wherein $R_{13}$ and $R_{14}$ are independently hydrogen or R as defined above;

$R_1$ and $R_2$ are independently hydrogen, $C_{1-20}$ alkyl, preferably $C_{1-10}$ alkyl, more preferably $C_{1-6}$ alkyl, most preferably $C_1$, $C_2$ or $C_3$ alkyl; $C_{1-20}$ alkyl sulfonate, preferably $C_{1-10}$ alkyl sulfonate, more preferably $C_{1-6}$ alkyl sulfonate, most preferably $C_1$, $C_2$, $C_3$, or $C_4$ alkyl sulfonate; $C_{1-20}$ alkyl carboxylic acid or carboxylate, preferably $C_{1-10}$ alkyl carboxylic acid or carboxylate, more preferably $C_{1-6}$ alkyl carboxylic acid or carboxylate, most preferably $C_1$, $C_2$, $C_3$, or $C_4$ alkyl carboxylic acid or carboxylate; $C_{1-20}$ alkyl amino or quaternized amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino or quaternized amino; aryl, benzyl, oligoethylene glycol, or polyethylene glycol;

$R_3$ and $R_1$ are independently hydrogen; hydroxyl; —$OR_5$; —$NH_2$; —$NHR_6$; —$NR_7R_8$, $C_{1-20}$ alkyl, preferably $C_{1-10}$ alkyl, more preferably $C_{1-6}$ alkyl, most preferably $C_1$, $C_2$ or $C_3$ alkyl; $C_{1-20}$ alkyl sulfonate, preferably $C_{1-10}$ alkyl sulfonate, more preferably $C_{1-6}$ alkyl sulfonate, most preferably $C_1$, $C_2$, $C_3$, or $C_4$ alkyl sulfonate; $C_{1-20}$ alkyl carboxylic acid or carboxylate, preferably $C_{1-10}$ alkyl carboxylic acid or carboxylate, more preferably $C_{1-6}$ alkyl carboxylic acid or carboxylate, most preferably $C_1$, $C_2$, $C_3$, or $C_4$ alkyl carboxylic acid or carboxylate; $C_{1-20}$ alkyl amino or quaternized amino, preferably $C_{1-10}$ alkyl amino or quaternized amino, more preferably $C_{1-6}$ alkyl amino or quaternized amino, most preferably $C_1$, $C_2$, $C_3$, or $C_4$ alkyl amino or quaternized amino; —COOH; —$CO_2^-$; or —$SO_3^-$; wherein $R_5$-$R_8$ are the same as R; oligoethylene glycol, or polyethylene glycol;

Z is carbon, nitrogen, sulfur, or oxygen, wherein if Y and/or Z is carbon, the carbon will be tetravalent having two substituents as defined above; if Y and/or Z is sulfur and/or oxygen; the sulfur and/or oxygen will be divalent; and if Y and/or Z is nitrogen, the nitrogen will be trivalent, having one substituent as defined above;

$R_{12}$ is H or D; and the benzene ring represented by dotted lines is optional;

In a preferred embodiment, the reduced cyanine dye is selected from Hydro-IR-676, Hydro-Cy3, Hydro-Cy5, Hydro-Cy7, Hydro-IR-783, Hydro-ICG, deuterated derivatives thereof, and combinations thereof. The structures of the hydrocyanine dyes are shown below:

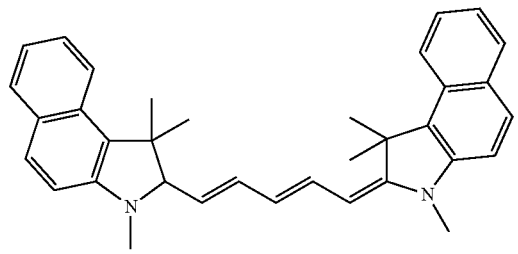

Hydro-IR-676

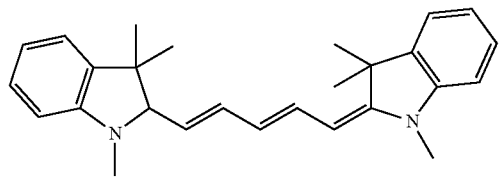

Hydro-Cy5

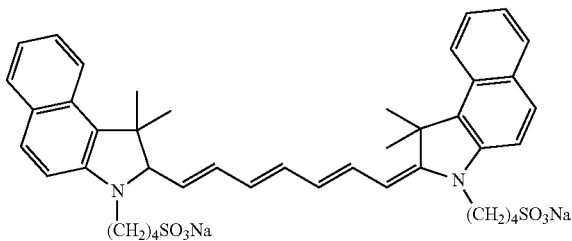

Hydro-ICG

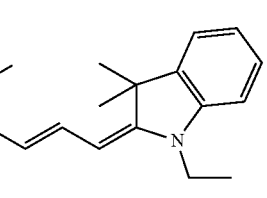

Hydro-Cy3

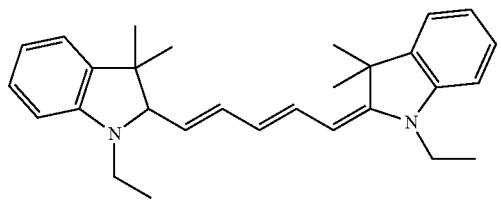

Hydro-Cy5

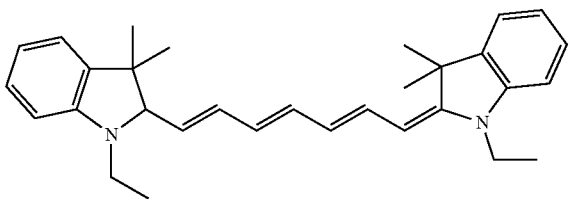

Hydro-Cy7

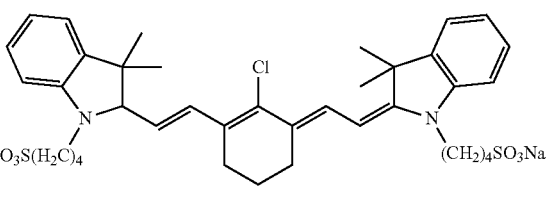

Hydro-IR-783

The structures of the corresponding deuterocyanine dyes are shown below. Oxidation of deuterocyanines generates the identical cyanine dye as their hydrogen analogues, allowing these probes to be used with existing protocols for ROS sensors.

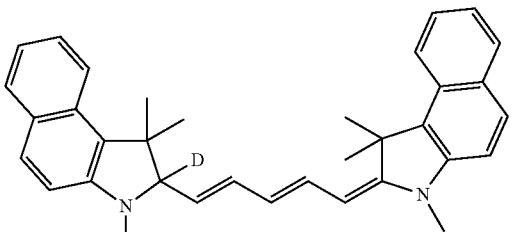

D-IR-676

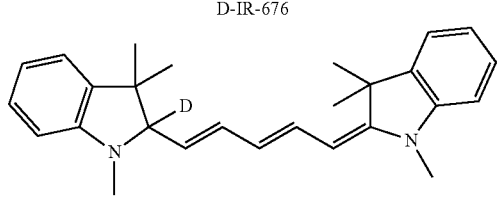

D-Cy5

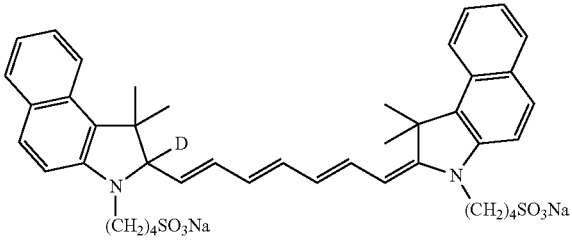

D-ICG

-continued

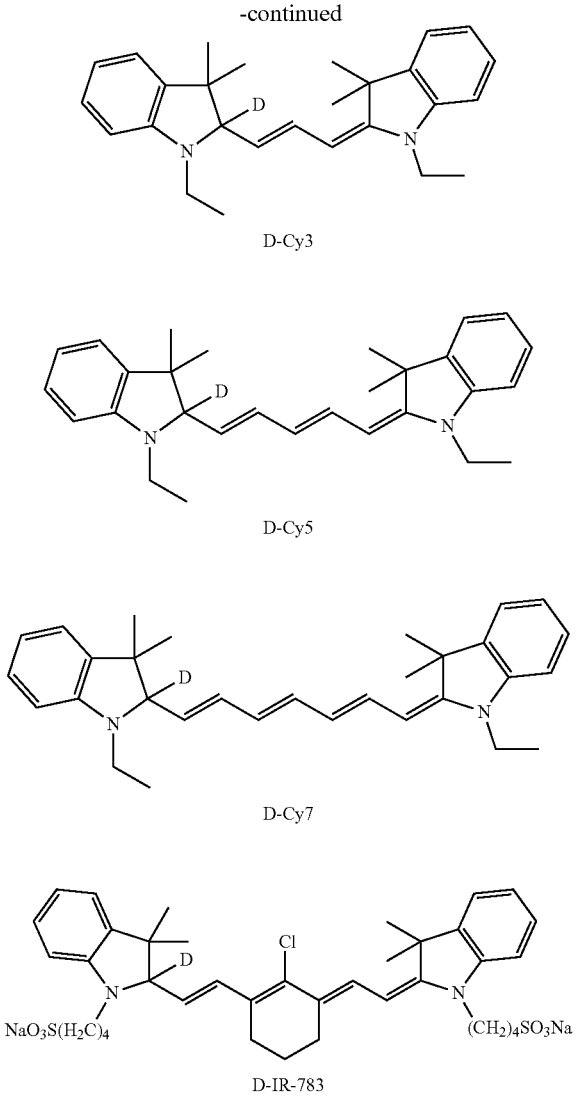

D-Cy3

D-Cy5

D-Cy7

D-IR-783

The reduced dyes described herein possess excellent stability to auto-oxidation, have tunable emission wavelengths, and picomolar to millimolar sensitivity. In one embodiment, the reduced dyes have at least picomolar to millimolar sensitivity. In a preferred embodiment, the reduced dyes have at least nanomolar (e.g., 1-50 nM, preferably 1-30 nM, more preferably 5-30 nM) to millimolar sensitivity to ROS. For example, the cyanine dyes described herein have emission wavelengths from 500-1100 nm (into the near infra-red), which is significantly higher than DHE or sulfonate ester-based dyes, and thus have potential for in vivo applications. The reduced dyes can be used to image ROS, such as hydroxide radical and superoxide, in serum, cell cultures, tissue explants, and in vivo.

Hydro-Cy3 is a membrane permeable molecule with the ability to diffuse into cells; however, after oxidation by intracellular ROS, it is fluorescent and membrane impermeable. Therefore, oxidized Hydro-Cy3 should accumulate within cells over producing ROS and detect intracellular ROS production. Hydro-Cy7 has properties suitable for measuring ROS in vivo. Hydro-Cy7 is also membrane permeable and should accumulate within cells and tissues that overproduce intracellular ROS. However, the high emission wavelength of oxidized Hydro-Cy7 ($\lambda_{ex}$=735 nm and $\lambda_{em}$=760 nm, which is in the near infra-red) should allow it to detect ROS in vivo. This an important feature of these dyes, since most fluorescent dyes are not effective in vivo.

As discussed in the Examples, hydrocyanines can detect at least nanomolar levels of ROS and emit in the near IR range (760-830 nm) in the case of Hydro-Cy7, Hydro-IR-783, and Hydro-ICG and their deuterated derivatives. At these emission wavelengths, in vivo, at a depth of 0.5 cm, a 2-3 order of magnitude reduction in sensitivity is anticipated, due to tissue attenuation and background fluorescence. The carotid artery is a superficial anatomic structure, which is located less than 0.5 cm from the skin surface. Therefore, the hydrocyanines described herein should be able to detect a target analyte, which is at micromolar concentrations, at least 0.5 cm from the skin surface. Moreover, many of the hydrocyanines described herein accumulate within cells after reaction with ROS, which may result in amplification of the signal due to multiples injections.

Charged and membrane impermeable molecules, such as Hydro-ICG, are suitable for measuring extracellular ROS production. The photochemical properties of exemplary dyes are shown in Table 3.

As discussed above, the hydrocyanines can also be unsymmetrical hydrocyanines, wherein the end groups are chemically different. The differences can include differences in the ring structure of the end group and/or unsymmetrical substitution of the end groups. For example, suitable unsymmetrical dyes include dues containing any two of the end groups shown in structures a-j. Exemplary unsymmetrical dyes are shown below:

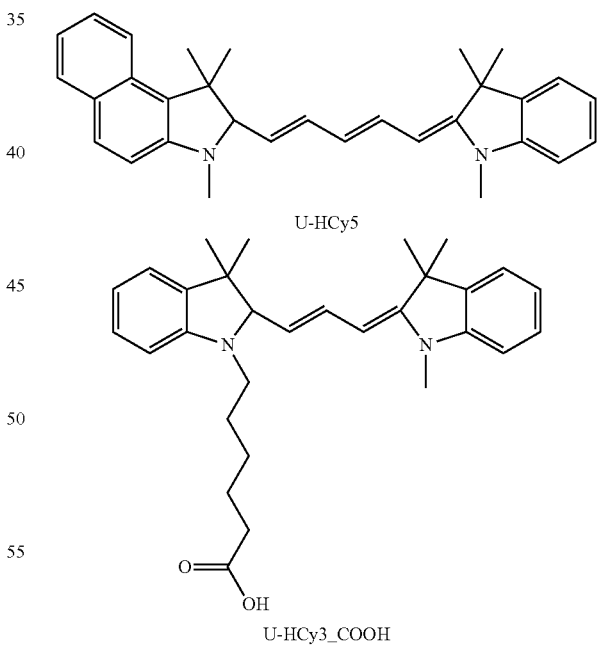

U-HCy5

U-HCy3_COOH

The sensitivity and specificity of the unsymmetrical hydrocyanines were similar/comparable with their symmetrical counterparts. The sensitivity of U-HydroCy3-COOH was similar to Hydro-Cy3 and U-HydroCy5 was similar to Hydro-Cy5 (all have nano molar sensitivity towards hydroxyl radical and superoxide anion radical and are highly specific for radicals).

i. Reduced Cyanines Having Improved Water Solubility

In one embodiment, the reduced cyanine is a hydrocyanine or deuterocyanine having improved water solubility. Hydrocyanines deuterocyanines can be modified to contain water-soluble functional groups which improve the water solubility of the dyes. Suitable functional groups include oligo- or polyalkylene oxide, such as oligo- or polyethylene, sulfonate groups, alkyl sulfonate groups, phosphoric or phosphonic acid residues, zwitterionic groups, carboxylate groups, and alkyl carboxylate groups. In a preferred embodiment, the functional groups are oligo- or polyethylene glycol. The number of repeat units is from about 1 to about 1,000, preferably from about 1 to about 500, more preferably from about 1 to about 100.

These groups are typically attached to the end group, such as the indole ring system, particularly the indole nitrogen. However, functional groups which improve the water solubility can be attached to the bridge and/or other parts of the dye, including other parts of the end group, such as an aromatic ring in a cyclic end group. In one embodiment, the functional groups, i.e., polyethylene glycol ("PEG") groups, are attached to the end groups of the cyanine dye, e.g., the indole ring system.

An exemplary functionalized dye is shown below:

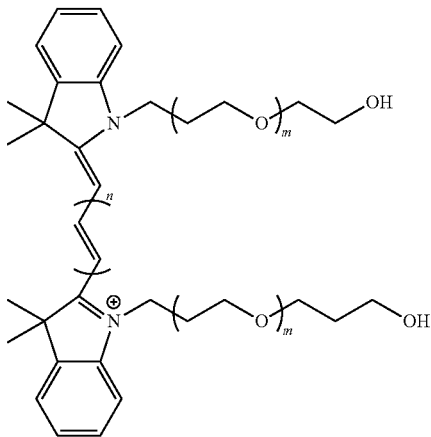

wherein n=0, 1, 2, or 3 and m is from 1-1000.

In another embodiment, the PEG groups are attached to both the nitrogen and the aromatic ring as shown below:

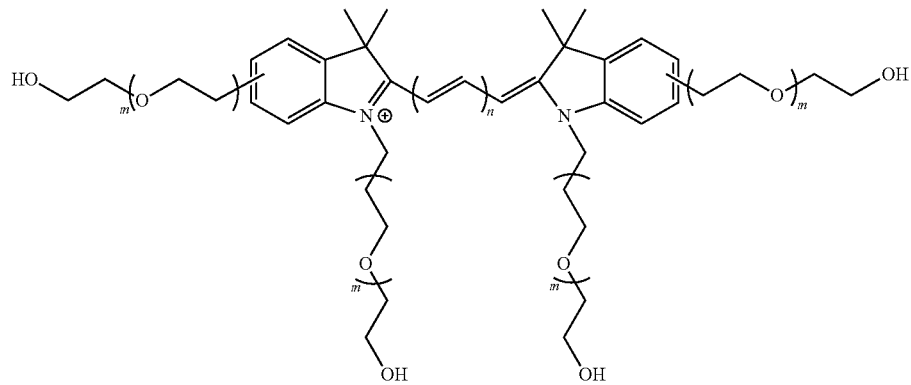

B. Other Reduced Dyes

As discussed above, any reduced dye can be used in the compositions and methods of making and using thereof described herein. In one embodiment, the reduced dye exhibits negligible fluorescence compared to the oxidized dye. In another embodiment, the reduced dye is membrane permeable and the oxidized dye is membrane impermeable. In yet another embodiment, the reduced dye and the oxidized dye are membrane impermeable.

The reduced dye can be a hydrodye (i.e., π-bond or bonds is reduced by hydrogen), a deuterodye (i.e., π-bond or bonds is reduced by deuterium), or a combinations thereof. Suitable π-bonds which can be reduced include, but are not limited to, iminium bonds (i.e., C=N bond), C=C bonds, C=S bonds, C=O bonds, and combinations thereof.

1. Deuterated Leuco Dyes

In one embodiment, the reduced dye is a deuterated leuco dye. As discussed above, DHE is inadequate as an ROS probe because of its poor stability due to auto-oxidation, particularly in aqueous solutions. Reducing ethydium bromide with sodium borodeuteride ($NaBD_4$) quantitatively converts DHE to D-DHE. Replacing the benzylic hydrogen with deuterium increases the stability of DHE by 4-6 fold, due to the primary kinetic isotope effect. This is shown in FIG. 2. FIG. 2a compares the stability of dihydroethydium (DHE) and deuterohydroethydium (D-DHE or DDE) in solution. FIG. 2b compares the stability of solid DHE and D-DHE. The presence of deuterium in DHE makes the molecules less susceptible to air oxidation, resulting in increased stability. Therefore, D-DHE may be a suitable compound for the detection of ROS. Other suitable deuterated leuco dyes which can be used include, but are not limited to, deuterated rhodamine, deuterated rhodamine analogs (such as the deuterated analog shown below), deuterated carboxy-2'7'-dichlorofluorescein diacetate (deuterated DCFDA), dideuterocalcein AM, dideuterorhodamine 6G, deuterolucigenin, deuteroRedoxSensor Red CC-1, deuterated 5-chloromethyl-2'7'-diehlorofluorescein diacetate (deuterated 5-CM-DCFDA), deuterated 6-chloromethyl-2'7'-dichlorofluorescein diacetate (deuterated 6-CM-DCFDA), combinations thereof, and combinations with one or more reduced cyanines.

Examples of these dyes are shown below:

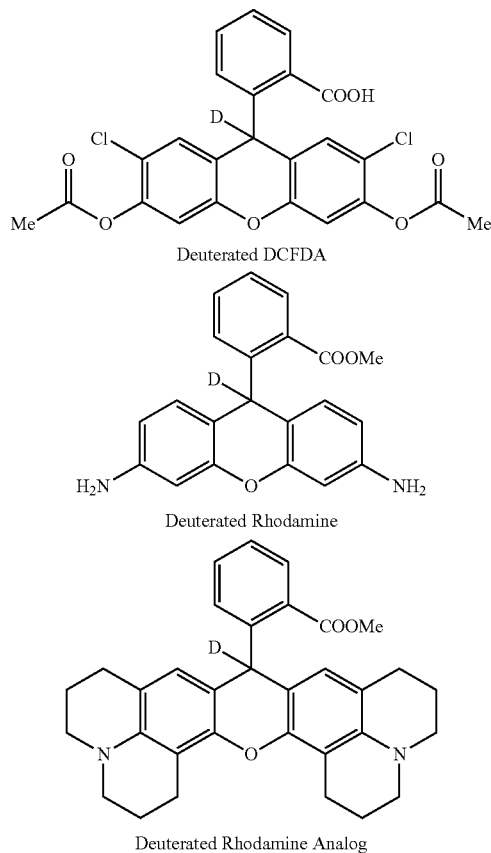

Deuterated DCFDA

Deuterated Rhodamine

Deuterated Rhodamine Analog

As discussed above with respect to the cyanines, other reduced dyes can be modified with water soluble functional groups to improve the water-solubility of the dye. The nature of the functional group and/or its location can be readily determined by one of ordinary skill in the art based on the functional groups present on the dye and the chemistry used to attached the functional groups.

III. Methods of Manufacture

A. Reduced Cyanine Dyes

Reduced dye can be prepared by reacting the oxidized dye with a suitable reducing agent. One of ordinary skill in the art can readily determine the appropriate reducing agent based on the n-bond to be reduced.

In one embodiment, reduced cyanine dyes can be prepared in a single step reaction by reacting the cyanine dye with a reducing agent to reduce the imine bond to the corresponding amine. A variety of reducing agents are known in the art. In one embodiment, the cyanine dye is reduced using sodium borohydride, $NaBH_4$. Sodium borohydride reduces aldehydes and ketones into alcohols, as well as the more reactive carboxylic acid derivatives acyl chlorides and thiol esters. However, unlike the more powerful reducing agent lithium aluminium hydride, sole use of NaBH4 with gentle reaction conditions will not reduce esters, amides, or carboxylic acids. $NaBH_4$ can also be used to reduce imine bonds to the corresponding amine (L. Blackburn, R. J. K. Taylor, *Org. Lett.*, 2001, 3, 1637-1639). The deuterocyanines can be synthesized by reacting the corresponding cyanine dye with a deuterated reducing agent, such as sodium borodeuteride. The synthesis and mechanism of reduction of a cyanine dye and oxidation by ROS is shown in Scheme 1.

Scheme 1. Reduction and Oxidation of Cyanine Dyes

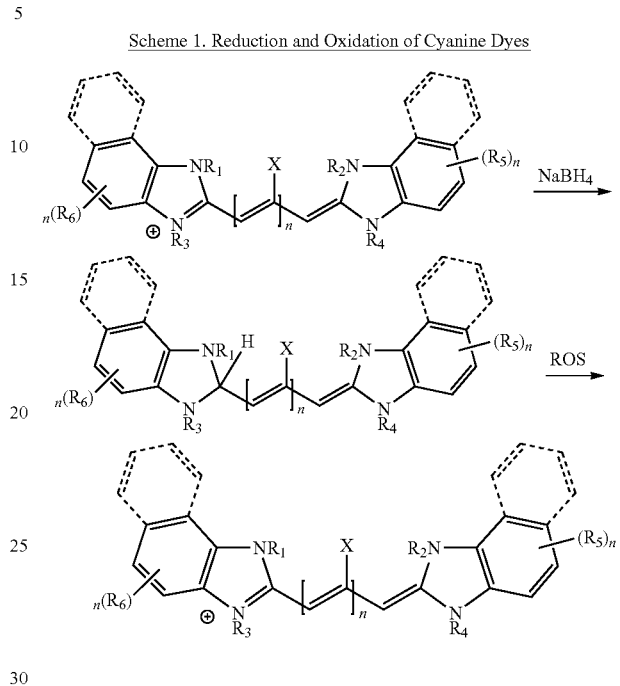

IV. Methods of Use

The compounds described herein can be used as diagnostic tools to detect and/or quantify ROS in a sample in vitro or to evaluate/detect a variety of diseases and disorders, or markers for diseases or disorders, characterized by the production or overproduction of ROS, in vivo. The fluorescence emitted by the oxidized dyes can be measured using fluorescence spectroscopy or fluorescence microscopy depending on the application. Exemplary methods of fluorescence microscopy include, but are not limited to, confocal laser scanning microscopy, total internal reflection fluorescence microscopy, histological analysis via fluorescence, flow cytometry, analyses using plate readers, such as fluorescence microplate readers, standard or mini fluormeters, or epifluorescence microscopes.

The general procedure for using the reduced dyes is as follows. One or more reduced dyes are administered in vivo or in vitro to contact cells, cell cultures, tissues, organs, serum, bodily fluids, etc. The one or more reduced dyes can be formulated with one or more carriers depending on the assay. The reduced dye(s) are incubated with the biological sample for a period of time sufficient for the reduced dye to react with reactive oxygen species present in the sample. After such time, the sample is analyzed for fluorescence intensity. The fluorescence intensity after incubation is compared to the fluorescence intensity of the reduced dye. An increase in the fluorescence intensity of the dye in the biological sample indicates oxidation of the dye, and thus presence of reactive oxygen species. The increased fluorescence can be measured/detected using the techniques listed above.

In Vivo Applications

Diagnosis of Diseases and Disorders or Markers for Diseases and Disorders In Vivo In general, up-regulation of reactive oxygen species reflects initiation of a disease or disease state. Therefore, the more fluorescence observed after administration of the reduced dye, the higher the propensity for the disease or disease state.

Exemplary diseases and disorders include, but are not limited to, carotid artery injuries, atherosclerosis, hypertension, cancers, diseases and disorders characterized by inflammation, radiation-induced late normal tissue damage (Zhao et al., *Curr. Med. Chem.*, 16(2), 130-43 (2009), tissue damages due to chemotherapy, reperfusion after ischemia, or transplantation, diabetes, such as type 1 diabetes (T1D) (Chen et al., *Ann. N.Y. Acad. Sci.*, 1150:157066, December 2008), neurodegenerative diseases, such as Alzheimer's disease (Block, *BMC Neurosci*, 9 Suppl. 2:S8, December 2008), Parkinson's disease (Zhou et al., *Ann. N.Y. Acad. Sci.*, 1147:93-104 December (2008)), ALA, and Huntington's disease (Stack et al., *Ann. N.Y. Acad. Sci.*, 1147:79-92 December (2008)), cerebrovascular disease (Chrissobolis et al., *Trends Mol. Med.*, 14(11), 495-502, November (2008)), cystic fibrosis (Pongnimitprasert et al., *Ann. Biol. Clin.*, 66(6), 621-9, November-December (2008)), chronic kidney disease and cardiovascular disease (Cachofeiro et al., *Kidney Int. Suppl.*, 111:S4-9, December (2008)), preeclampsia (Gilbert et al., *Expert. Rev. Cardiovasc. Ther.*, 6(10), 1367-77, November (2008)), and ophthalmic diseases. The compounds described herein can also be used as contrast agents and as markers for imaging biomolecules in vivo, such as through photoacoustic imaging.

Detection of ROS Production in Carotid Artery Injuries

The overproduction of ROS in the carotid artery is pathologically linked to the growth and rupture of carotid artery atherosclerotic plaques, which cause strokes. Increased ROS production is necessary for the development of carotid artery atherosclerosis in mice, rat, and rabbit models. ROS has been implicated in many of the key pathological features of atherosclerosis, such as endothelial dysfunction, angiogenesis, smooth muscle cell overgrowth, endothelial cell apoptosis, expression of inflammatory proteins, vascular remodeling, and the activation of MMPs, all of which have been associated with plaque ruptures. Contrast agents which can image ROS production in the carotid artery have the potential to diagnose active atherosclerotic lesions in the carotid artery and identify patients who are at risk of developing strokes.

The rate of superoxide production in vivo in carotid arteries, following vascular injury, has been measured in rats ex vivo at a rate of 2-3 nmols/mg wet carotid tissue/minute and is increased by a factor of 2-3 in most animal models of carotid injury. This is an extremely high rate of ROS production, corresponding to micromoles/mL wet carotid tissue/minute and should be detectable by the hydrocyanines described herein, even after attenuation, in view of the results described in the Examples.

As discussed in the Examples, hydrocyanines can detect nanomolar levels of ROS and emit in the near IR range (760-830 nm) in the case of Hydro-Cy7, Hydro-IR-783, and Hydro-ICG and their deuterated derivatives. At these emission wavelengths, in vivo, at a depth of 0.5 cm, a 2-3 order of magnitude reduction in sensitivity is anticipated, due to tissue attenuation and background fluorescence. The carotid artery is a superficial anatomic structure, which is located less than 0.5 cm from the skin surface. Therefore, the hydrocyanines described herein should be able to detect a target analyte, which is at micromolar concentrations, 0.5 cm from the skin surface. Moreover, many of the hydrocyanines described herein accumulate within cells after reaction with ROS, which may result in amplification of the signal due to multiples injections.

Positron Emission Tomography (PET) Contrast Agents

The hydrocyanines and/or deuterocyanines described herein can be used as PET contrast agents. For example, cyanine dyes can be radiolabeled with tritium or $^{11}C$ via alkylation using the corresponding labeled alkyl iodides. The labeled cyanine dye can be reduced using sodium borohydride or sodium borodeuteride as described below to form the corresponding hydrocyanine or deuterocyanine suitable for imaging ROS.

Imaging of Biomolecules In Vivo

One of the benefits of the hydro- and/or deuterocyanines for imaging ROS is that they oxidize to form cyanine dyes, a family of dyes which possess excellent chemical and physical properties for in vivo fluorescence imaging. Cyanine dyes have been used extensively for imaging biomolecules in animal and humans because of their high emission wavelengths, high photostability, and high quantum yields. For example, Cy-5 conjugated to cell ligands can detect picomolar/nanomolar levels of target analyte, in vivo, in superficial anatomic structures, such as tumors. The cyanine dye, indocyanine green (ICG), has been used in humans for imaging angiogenesis in the eyes and has been investigated for breast cancer imaging in optical inherence tomography imaging. The use of Cy-5 and ICG for in vivo imaging demonstrates the biocompatibility of cyanine dyes (and thus the reduced cyanine dyes).

As discussed above, one of the advantages of the reduced dyes is that, in the case of hydrocyanines, the reduced molecules are membrane permeable and thus accumulate in cells and tissue. Upon reaction with ROS, the reduced molecules oxidize to cyanine dyes resulting in a substantial increase in fluorescence. The oxidized cyanines are membrane impermeable and thus are trapped within the cells and tissue. The use of reduced dyes allows one to detect/image the overproduction of ROS in specific cells and/or tissues.

Photoacoustic Imaging

Photoacoustic imaging is based on the photoacoustic effect. In photoacoustic imaging, non-ionizing laser pulses are delivered into biological tissues (when radio frequency pulses are used, the technology is referred to as thermoacoustic imaging). Some of the delivered energy will be absorbed and converted into heat, leading to transient thermoelastic expansion and thus wideband (e.g. MHz) ultrasonic emission. The generated ultrasonic waves are then detected by ultrasonic transducers to form images. It is known that optical absorption is closely associated with physiological properties, such as hemoglobin concentration and oxygen saturation. As a result, the magnitude of the ultrasonic emission (i.e. photoacoustic signal), which is proportional to the local energy deposition, reveals physiologically specific optical absorption contrast. 2D or 3D images of the targeted areas can then be formed. Reduced dyes, such as hydrocyanine or deuterocyanines, would be used for PA imaging in the identical way that they are used for fluorescent imaging. The dyes are injected directly on the potential diseased tissue, or given intravenously, and then imaged by photoacoustic imaging.

Formulations for In Vivo Applications

For in vivo applications, the formulations can be administered by a variety of routes. Typically, the compounds are formulated for parenteral administration including, but not limited to, intravenous, intraarterial, intramuscular, intraperitoneal, subcutaneous, intradermal, infusion, subconjunctive, and intracatheter (e.g., aurologic delivery), as well as administration via external scopic techniques such as, for example, arthroscopic or endoscopic techniques.

The amount of reduced dye is the minimum amount required to yield detectable signal in the sample within a reasonable time, with minimal background fluorescence. The exact concentration of reduced dye to be used is dependent upon the experimental conditions and the desired results, and optimization of experimental conditions is typically required to determine the best concentration of reduced to be used in a given application. The concentration of reduced dye typically ranges from nanomolar to millimolar, preferably from nanomolar to micromolar. The reduced dye concentrations are readily determined from methods known in the art for use of similar compounds under comparable conditions for the desired optical response. In one embodiment, the amount of dye is from about 50 µg/kg to about 50 g/kg, preferably from about 50 µg/kg to about 10 g/kg, more preferably from about 50 µg/kg to about 1 g/kg, most preferably from about 50 µg/kg to about 0.1 g/kg.

The compounds will typically be combined with one or more excipients, additives, or carriers. As used herein, the "carrier" is all components present in the pharmaceutical formulation other than the reduced dyes. The term "carrier" includes, but is not limited to, solvents, suspending agents, dispersants, buffers, pH modifying agents, isotonicity modifying agents, preservatives, antimicrobial agents, and combinations thereof. Other additives include those useful for processing or preparation of the composition, can aid in the incorporation or stability of the compositions, or can be useful in modifying performance of the composition.

The compositions can contain other excipients including any number of other medically or pharmaceutically acceptable agents such as preservatives, lipids, fatty acids, waxes, surfactants, plasticizers, porosigens, antioxidants, bulking agents, buffering agents, chelating agents, cosolvents, water-soluble agents, insoluble agents, metal cations, anions, salts, osmotic agents, synthetic polymers, biological polymers, hydrophilic polymers, polysaccharides, sugars, hydrophobic polymers, hydrophilic polymers, and combinations thereof.

The compositions can be administered to specific locations (e.g., local delivery) including, but not limited to, intrathecal, intracardiac, intraosseous (bone marrow), stereotactic-guided delivery, infusion delivery, CNS delivery, stereo-tactically administered delivery, orthopaedic delivery (for example, delivery to joints, into bone and/or bone defects, cardiovascular, inter- and intra- and para-ocular (including intravitreal and scleral and retrobulbar and sub-tenons delivery), as well as delivery to any multitude of other sites, locations, organs, etc.

In Vitro and Ex Vivo Applications

The reduced dyes, and compositions containing the reduced dyes, can be used for a variety of in vitro and/or ex viva assays. The dye can be used for single cell imaging or to assay a cell suspension. For example, the dye can be loaded into cells by incubating the dye(s) with the cells for a sufficient period of time, for example, 20 minutes. Specific assays include live organ cultures as well as cell cultures assays in which DHE is used. DHE has been used for detection of oxidative activities in viable cells, including respiratory burst in phagocytes, superoxide generation in mitochondria or as a vital stain in flow cytometry for imaging and analysis of intact cells. It has also been shown to exhibit increased fluorescence in various models of apoptosis. DHE can be used as a generic substrate for the fluorimetric detection of oxidases, such as peroxidase; for the detection of cytochromes; and for the detection of free radical production in brain tissue.

Formulations for In Vitro and Ex Vivo Applications

The reduced dyes described herein are typically solids at room temperature. Therefore, the compounds will generally be dissolved or suspended in carrier for administration. The exact concentration of reduced dye to be used is dependent upon the experimental conditions and the desired results, and optimization of experimental conditions is typically required to determine the best concentration of reduced to be used in a given application. The concentration of reduced dye typically ranges from nanomolar to millimolar, preferably from nanomolar to micromolar. The reduced dye concentrations are readily determined from methods known in the art for use of similar compounds under comparable conditions for the desired optical response. Typically, the concentration of the dye contacted with the cells is from about 1 µM to about 100 µM. However, the specific concentration can be readily determined based on the assay being performed. In general, the compounds described herein will be dissolved or suspended in an appropriate solvent suitable for the intended application. Suitable solvents include aqueous solvents, such as water, PBS, saline; organic solvents, such as DMSO and alcohols, and combinations thereof. The dyes can be encapsulated in various nanostructures to improve cell delivery. Suitable nanostructures include, but are not limited to, liposomes, microparticles, such as polymeric microparticles, and micelles, such as polymeric micelles formed from block copolymers.

V. Kits

The term "kit" as used refers to a packaged set of related components, typically one or more compounds or compositions. The kit include one or more reduced dyes, one or more carriers suitable for in vitro and/or in vivo applications, and one or more containers to store the one or more reduced dyes and/or one or more carriers, such as solvents, buffers, stabilizers, pH adjusting agents, etc. The kit optionally contains instructions for how to prepare the one or more reduced dyes, or a composition containing the one or more reduced dye, how to administer the dye or composition containing the dye, and how to detect oxidation of the dye (e.g., excitation wavelength and emission wavelength). In a preferred embodiment, the kit contains instructions for performing an assay that detects the presence of one or more reactive oxygen species. The kit may further contain one or more pieces of equipment to administer the dye, or composition containing the dye including, but not limited to, syringes, pipettes, pipette bulbs, spatulas, vials, syringe needles, and combinations thereof.

EXAMPLES

Example 1

Representative Procedure for the Synthesis of Hydrocyanines

Cy3 (100 mg, 0.2 mmol) was dissolved in 5 ml of methanol. The mixture was placed in a 4-drum vial covered with aluminum foil. Sodium borohydride, $NaBH_4$ (3 mg, 0.08 mmol in 0.5 ml methanol), was added dropwise to the purple Cy3 solution. After the addition of $NaBH_4$, the mixture was stirred for 10 minutes, generating a colorless solution. The reaction mixture was stirred an additional 10 minutes before removing the solvent under reduced pressure. The resulting solid was dissolved in 10 ml of dichloromethane ($CH_2Cl_2$) and 5 ml water and vigorously shaken. The organic layer was extracted with additional dichloromethane (5 ml×2), dried over anhydrous sodium sulfate, and the solvent was removed under reduced pressure. The reduced dye was used without additional purification.

Reduced versions of Cy5, IR-676, Cy7, and ICG were prepared using the procedure described above, or a modified version thereof. The reduction of the imine was confirmed by $^1$H and $^{13}$C NMR. A summary of the yields of the various reduced cyanines is shown in Table 1.

TABLE 1

Isolated yields of various hydrocyanines

| Hydrocyanine | Isolated Yield (%) |
|---|---|
| Hydro-Cy3 | 97 |
| Hydro-Cy5 | 95 |
| Hydro-IR-676 | 93 |
| Hydro-Cy7 | 95 |
| Hydro-IR-783 | 93 |
| Hydro-ICG | 93 |

The hydrocyanines exhibited negligible fluorescence due to reduction of the iminium cation which results in the disruption of the π-conjugation.

Deuterocyanines were prepared using the produced above except sodium borohydride was replaced with sodium borodeuteride. Deuterorhodamine was prepared in a similar manner. A comparison of the stability of the hydrocyanines and their deuterated counterparts is shown in Table 2.

TABLE 2

Deuteration increases the stability to aerial-oxidation of superoxide and radical oxidant probes

| Oxidized Forms 1-5 | Reduced Forms 6-10 (H/D) | X | Yield [%]$^a$ | $T_{1/2}$ [h] | $k_H/k_D$ |
|---|---|---|---|---|---|
| Cy3 (3) | Hydro-Cy3 (7H) / Deutero-Cy3 (7D) | H / D | 97 / 96 | 36 / 84 | 3.7 |
| Cy5 (4) | Hydro-Cy5 (8H) / Deutero-Cy5 (8D) | H / D | 95 / 95 | 31 / 80 | 4.1 |
| Cy7 (5) | Hydro-Cy7 (9H) / Deutero-Cy7 (9D) | H / D | 95 / 94 | 30 / 82 | 4.6 |
| Rhodamine (6) | Hydrorhodamine (10H) / Deuterorhodamine (10D) | H / D | 93 / 93 | 1.5 / 2.1 | 2.1 |

Example 2

Sensitivity of Reduced Dyes to Reactive Oxygen Species In Vitro

Hydroxide Radical

Hydroxide radicals were generated in situ by reacting hydrogen peroxide with $Fe^{2+}$. Various quantities of hydrogen peroxide ($H_2O_2$) stock solutions were added to a solution of hydrocyanine in methanol to generate hydrogen peroxide concentrations from about 2 to about 30 nM. Aqueous $Fe^{2+}$ (1 μM) was added to the reduced dye/$H_2O_2$ solution to generate a 200 nM concentration. The resulting solution was kept at ambient temperature for 5 minutes and the fluorescence intensity was measured ($\lambda_{ex}/\lambda_{em}$) against a reagent blank (control solution containing only reagent) simultaneously.

Superoxide

Superoxide ($O_2^-$) was created by the enzymatic reaction of XA/XO (10 lm/10 mU) at 25° C. for 5 min (XA=Xanthene, XO=Xanthene oxidase). XA/XO (10 lm/10 mU) was added to buffered solutions of Hydro-Cy3 (10 mM) maintained in a 37° C. water bath. The fluorescence emission of each reaction mixture was measured at 5-min intervals against a reagent blank using a fluorescence spectrometer. In some cases solid $KO_2$ (1 mg) or $KO_2$ dissolved in DMSO was added to a Hydro-IR-786 solution in methanol or DMSO and the emission spectra was recorded. Alternatively, hydro-IR-786 (2 mg) was dissolved in 1 mL of ethanol and 50 μL of 2.0 mM $KO_2$ solution (7 mg $KO_2$ was dissolved in 10 mL dimethylsulfoxide) was added and stirred for 15 min before recording the emission spectra.

A summary of the photochemical properties of various hydrocyanines, after reaction with superoxide, is shown in Table 3.

TABLE 3

Summary of photochemical properties of various hydrocyanines

| Hydrocyanine | Fold Increase in Intensity[a] | $\lambda_{ex}/\lambda_{em}$ nm[b] |
|---|---|---|
| Hydro-Cy3 | 118 | 535/560 |
| Hydro-Cy5 | 97 | 635/660 |
| Hydro-IR-676 | 100 | 675/693 |
| Hydro-Cy7 | 104 | 735/760 |
| Hydro-IR-783 | 83 | 765/800 |
| Hydro-ICG | 86 | 750/830 |

[a]Fold increase was calculated by dividing the fluorescent intensity of oxidized hydrocyanine with the hydrocyanine fluorescence intensity. Concentrations of hydrocyanines and oxidized hydrocyanines were 7.5 μM in 1 mL methanol. Hydrocyanines were oxidized with 20 μL of DMSO containing 20 mM $KO_2$.
[b]Excitation and emission wavelengths for the corresponding oxidized products The hydrocyanines exhibited negligible fluorescence due to reduction of the iminium cations. However, after reaction with either superoxide or hydroxyl radical, the various hydrocyanines fluoresced at 560 nm, 660 nm, 760 nm, 800 nm, and 830 nm, respectively (see Table 2).

Figure 3B:
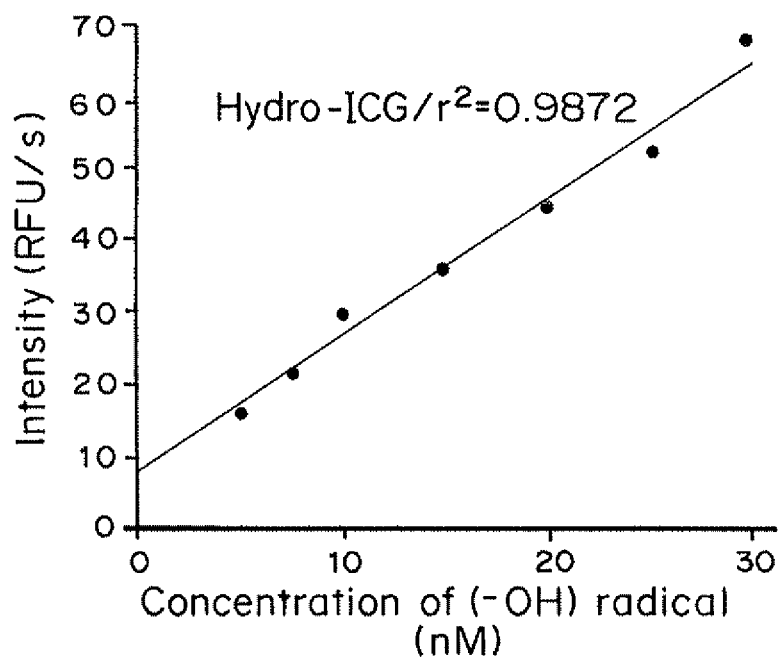
FIG. 3b is a graph showing the intensity of the fluorescence of hydro-ICG (RFU/s) as a function of hydroxyl radical concentration (nM).

Hydro-Cy3 and Hydro-Cy7 exhibited nanomolar sensitivity toward hydroxyl radical in vitro having linear relationships ($r^2=0.99$) between fluorescence intensity and the hydroxyl radical in the 1-50 nM range (see FIG. 3a). For example, Hydro-Cy3 detected 5 nM concentration of hydroxide radical, and generated a linear concentration curve against hydroxide radical in the concentration range of 5-50 nM hydroxide radical. This is significantly better than dihydroethydium (DHE), which had an $r^2$-value of 0.36 in this concentration range (see FIG. 3a). Hydro-ICG can detect ROS in 100% human serum with nanomolar sensitivity (see FIG. 3b). This measurement was carried out using 100 μM of Hydro-ICG at 25° C. The hydroxide radical was generated using the procedure described above. This demonstrates that hydrocyanines can compete effectively with biomolecules, such as protein thiols, for ROS.

Figure 4:
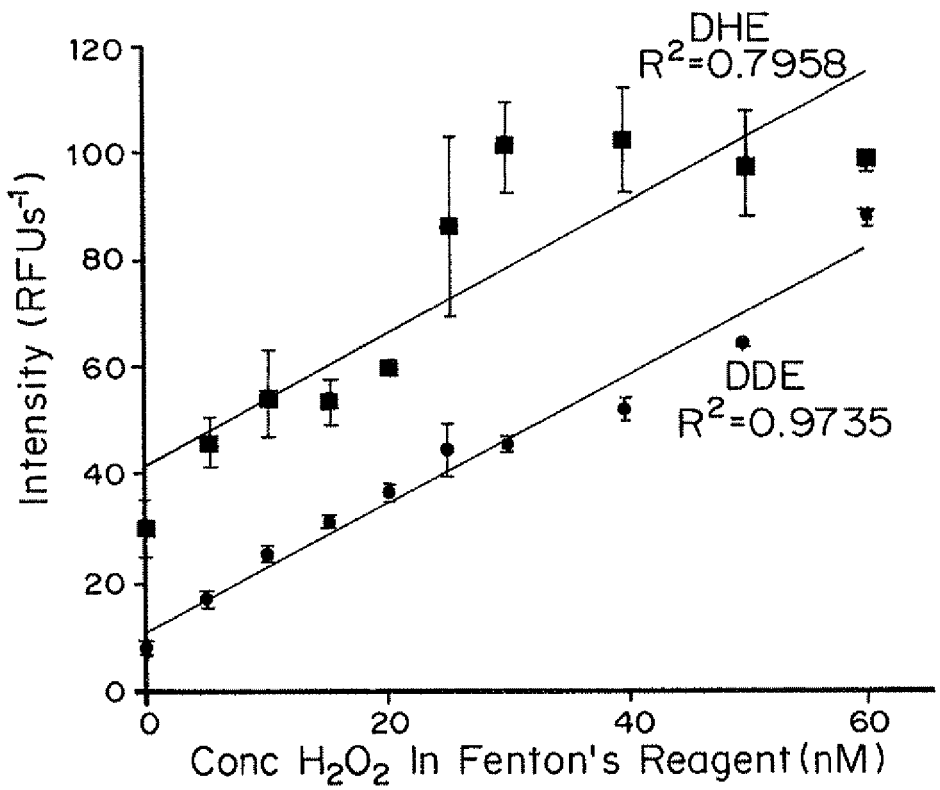
FIG. 4 is a graph comparing the intensity of the fluorescence (relative fluorescence units, RFU/S) of DHE and DDE as a function of hydrogen peroxide concentration (nM) in Fenton's reagent.

The sensitivity of deuterohydroethydium (D-DHE or DDE) was evaluated in the same manner. A 50 μM solution of DHE or D-DHE (DDE) in PBS buffer was treated with Fenton's reagent (using 1-60 nM $H_2O_2$ with $Fe^{2+}$) and the fluorescence of the oxidized product was measured. The results are shown in FIG. 4. FIG. 4 demonstrates that D-DHE can accurately measure ROS in the concentration range of 5-60 nM, having a linear relationship between fluorescence intensity and hydrogen peroxide concentration in the Fenton's reagent ($r^2=0.97$). In contrast, DHE was incapable of accurately detecting ROS in this concentration range and had an $r^2$-value of 0.79. Moreover, the average percent standard deviation of D-DHE was significantly smaller than that of DHE, which will improve the relative efficacy of D-DHE.

Example 3

Specificity of Hydro-Cy7 to ROS

A 50 μm Hydro-Cy7 solution was prepared in phosphate buffered saline (PBS) containing 1% methanol. Various reactive oxygen species were added to the 50 μm Hydro-Cy7 solution, at an equimolar ratio to Hydro-Cy7, and the fluorescence intensity was recorded after incubating 5 minutes at 25° C. Superoxide ($O_2^-$) was added as solid $KO_2$. Stock solutions of hydrogen peroxide, t-butyl hydrogen peroxide (TBHP), hypochlorite, 3-morpholinosydnonimine (SIN-1), glutathione (GSH), and 1,4-hydroquinone were prepared and added to the Hydro-Cy7 solution to generate a final concentration of 50 μM. 3-(aminopropyl)-1-hydroxy-3-isopropyl-2-oxo-1-triazene (NOC-5, 1 mM) was prepared as a 10 mM sodium hydroxide solution and added to the Hydro-Cy7 solution to generate a final concentration of 50 μM. The hydroxide and butoxy radicals were generated in situ by reacting hydrogen peroxide and t-butylperoxide with $Fe^{2+}$. A 50 μM Hydro-Cy7 solution, in PBS, containing 500 μM $Fe^{2+}$ was prepared and either hydrogen peroxide or t-butyl hydrogen peroxide was added to this solution to generate a final concentration of 50 μM.

Figure 5:
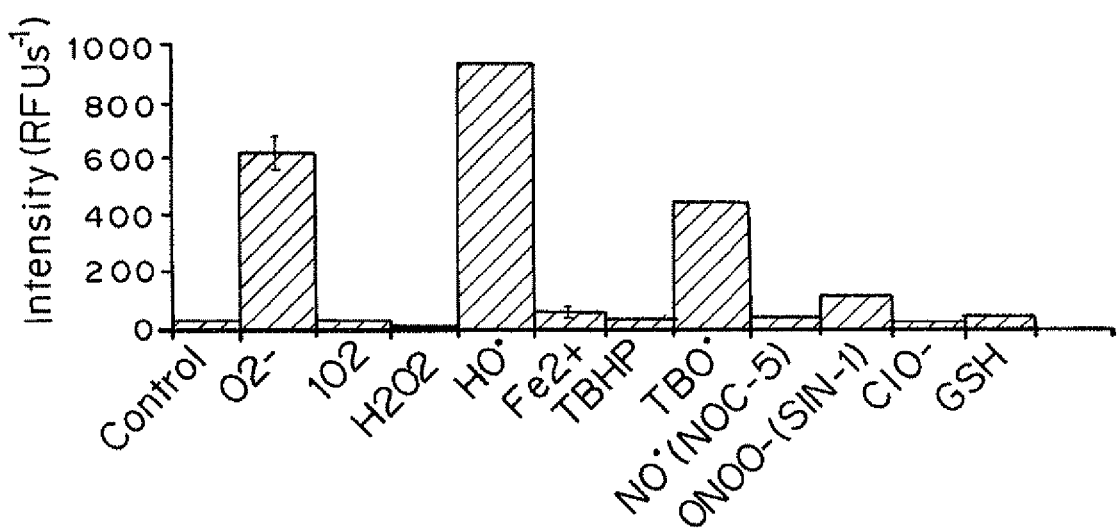
FIG. 5 is a bar graph showing the sensitivity of hydro-Cy7 (intensity, RFU/s) to various reactive oxygen species.

Hydro-Cy7 exhibited specificity for superoxide and hydroxyl radical compared to other reactive oxygen species found in cells. FIG. 5 shows the ROS specificity for hydro-Cy7. Hydro-Cy7 can detect superoxide, hydroxyl radical, and butoxy radical and has some sensitivity to hydrogen peroxide and reactive nitrogen species ($ONOO^-$). A similar specificity profile was observed for Hydro-Cy3.

Example 4

Stability of Reduced Dyes to Autooxidation

Figure 6:
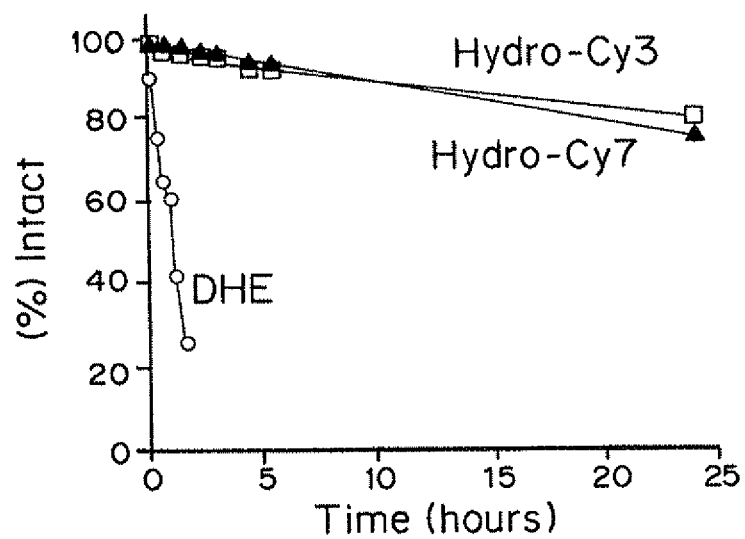
FIG. 6 is a graph comparing the stability to auto-oxidation (% intact) of hydro-Cy3, hydro-Cy7, and DHE as a function of time (hours).

A solution of hydrocyanine in PBS buffer (pH 7.4) was placed in an Eppendorf tube and placed in a 37° C. water bath. Stability was measured by monitoring the formation of the oxidation product using fluorescence spectroscopy over a 24 hour period. The excitation and emission wavelengths for the hydrocyanines prepared in Example 1 are shown in Table 2. The excitation and emission wavelengths for DHE were 515 and 590 nm. The results are shown in FIG. 6. Hydro-Cy3 and Hydro-Cy7 have a half-life of approximately 3 days in aqueous pH 7.4 buffer compared to DHE, which has a half-life of only 30 minutes; a difference of two orders of magnitude. Similar results were obtained with Hydro-Cy5.

The stability of deuterocyanines was evaluated in the same manner. Reducing ethydium bromide with sodium borodeuteride ($NaBD_4$) quantitatively converts DHE to D-DHE. Replacing the benzylic hydrogen by deuterium increases the stability of DHE by 4-6 fold, due to the primary kinetic isotope effect. This is shown in FIG. 2. FIG. 2a compares the stability of dihydroethydium (DHE) and deuterohydroethydium (D-DHE or DDE) in solution. FIG. 2b compares the stability of solid DHE and D-DHE. The presence of deuterium in DHE makes the molecules less susceptible to air oxidation, resulting in increased stability.

Example 5

Detection of ROS by Reduced Dyes in Rat Aortic Smooth Muscle (RASM) Cells

Hydrocyanines

The ability of hydrocyanines to detect ROS in rat aortic muscle (RASM) cells during angiotensin (Ang) II mediated cell signaling was evaluated using fluorescence spectroscopy. Ang II-mediated ROS production in aortic smooth muscle cells has been implicated in the development of atherosclerosis and hypertension. Fluorescence spectroscopy showed that hydrocyanine (e.g., Hydro-Cy3) detected ROS production in RASM cells during Ang II-mediated cell signaling. For example, RASM cells incubated with Ang II and hydrocyanine (Hydro-Cy3, 100 µM) displayed an intense intracellular fluorescence, whereas RASM cells incubated with Hydro-Cy3 alone displayed significantly less fluorescence. Application of the superoxide dismutase mimetic TEMPOL resulted in a dramatic decrease in fluorescence from RASM cells treated with Hydro-Cy3 and Ang II, demonstrating that the cellular fluorescence was due to intracellular ROS production. Administration of DHE under the same conditions failed to detect ROS, likely due to its high auto-fluorescence and poor stability.

Administration of the hydrocyanine caused no cellular toxicity under the experimental conditions described above nor at higher concentrations (1 mM), as determined by the trypan blue cell viability assay.

Deuterocyanines

RASM cells were stimulated with Ang II and then incubated with 50 µM of either hydro-Cy3 or deutero-Cy3 for 10 minutes. Deutero-Cy3 is significantly more efficient than hydro-Cy3 at detecting intracellular ROS. RASM cells incubated with hydro-Cy3 generated relatively higher amounts of background fluorescence, compared to deutero-Cy3. It is evident from fluorescence measurements that hydro-Cy3 is sensitive enough to detect even the ROS production by normal cells, causing relatively higher background fluorescence. On the other hand, because of the tuned reaction rate, deutero-Cy3 can only detect the overproduction of ROS during Ang-II mediated ROS over-production. Therefore, RASM cells incubated with deuteron-Cy3 have negligible background fluorescence and generate a significant increase in fluorescence after stimulation with Ang II. Importantly, application of the superoxide dismutase mimetic TEMPOL resulted in a complete loss in fluorescence from RASM cells treated with deuteron-Cy3 and Ang II, demonstrating that deuteron-Cy3 can specifically image the over-production of intracellular ROS production.

D-DHE (DDE)

The ability of D-DHE to detect ROS in rat aortic muscle (RASM) cells during angiotensin (Ang) II mediated cell signaling was evaluated using fluorescence spectroscopy. A comparative cell-culture study between DHE and D-DHE was conducted to evaluate the ability of DHE and D-DHE to detect ROS production in rat aortic smooth muscle (RASM) cells, during angiotensin (Ang) II mediated cell signaling.

RASM cells were isolated as described above, stimulated with Ang II and then incubated with 10 µM of either D-DHE or DHE for 10 minutes and imaged by fluorescent microscopy. DDE was significantly better than DHE at detecting intracellular ROS produced during cell signaling. For example, RASM cells incubated with DHE generated a large amount of background fluorescence, presumably due to the high auto-oxidation rate of DHE. Stimulation of RASMs with Ang II was not detected with DHE due to the high level background fluorescence. In contrast, RASM cells incubated with D-DHE had very low levels of background fluorescence and generated a significant increase in fluorescence after stimulation with Ang II.

Application of the superoxide dismutase mimetic TEMPOL resulted in a dramatic decrease in fluorescence from RASM cells treated with D-DHE and Ang II, demonstrating that the cellular fluorescence was due to intracellular ROS production. For DHE, the background fluorescence from aerial oxidation significantly hindered its effectiveness in the detection of ROS in cell culture. In contrast, the higher stability of D-DHE allowed for the accurate detection of the overproduction of ROS during the Ang-II mediated signaling event.

Example 6

Detection of ROS by Hydrocyanines in Live, Explanted Mouse Aortas

The ability of hydrocyanines to detect ROS from live, explanted mouse aortas, after lipopolysaccharide endotoxin (LPS) stimulation to produce ROS, was evaluated. The detection of ROS in live tissue can provide information about ROS production in a physiological environment that closely resembles in vivo conditions. C57B1/6 mice were treated with either 16 mg/kg lipopolysaccharide endotoxin (LPS) or PBS for 16 hours and then euthanized. The aortas of the mice were isolated and incubated with either Hydro-Cy3 or Hydro-Cy3+TEMPOL for 15 minutes. Sections of the aorta were made, fixed with 10% formalin, and mounted en face. Confocal fluorescent imaging showed that hydrocyanines can image ROS production in live tissue explants. For example, mice incubated with LPS and Hydro-Cy3 displayed significantly higher fluorescence intensity than mice treated with PBS and Hydro-Cy3.

Integrated total fluorescence intensity from the histology slides demonstrated that hydrocyanines can detect ROS in tissue. For example, the fluorescence intensity of the LPS-treated slide was 183.2 RFU/S compared to 46.9 RFU/S in the PBS-treated mice. Application of TEMPOL (small molecule cell-permeable superoxide dismutase mimetic1, which attenuates superoxide anion and peroxynitrite-induced inflammation) to mouse aortas, treated with LPS, reduced the fluorescence to control levels. The integrated fluorescence intensity from TEMPOL-treated aortas was 34.9 RFU/S demonstrating that hydrocyanine fluorescence was due to ROS production.

Administration of DHE under the same conditions failed to detect ROS, due likely to the its high auto-fluorescence and poor stability.

Example 7

In Vivo Detection of ROS

Figure 7:
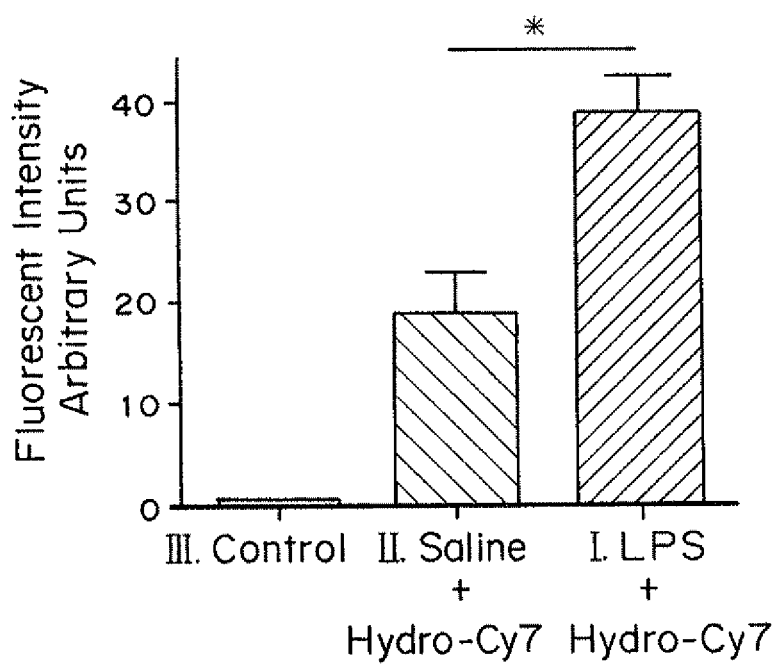
FIG. 7 is a graph comparing the fluorescent intensity (RFU/S) of hydro-Cy7+saline (white bar) and hydro-Cy7+LPS (dark bar).

The ability of hydrocyanines to image ROS production, in vivo, generated by activated macrophages and neutrophils, in an LPS model of acute inflammation was evaluated. Nine C57B1/6 mice were divided into three groups: Group I was given an intraperitoneal (i.p.) injection of LPS (1 mg in 400 µL saline); Group II was given saline (400 µL); and Group III was untreated. After 6 hours, the mice were anaesthetized, their abdominal fur was removed, and the LPS and saline treated mice were injected i.p. with Hydro-Cy7 (5 nanomoles in 50 µL methanol). The mice were images as triplets, one from each group, using a Kodak FX in vivo images with a 700 nm excitation laser and a 790 nm emission filter. Imaging showed that mice treated with LPS and Hydro-Cy7 had greater fluorescence intensity compared to mice treated with saline and Hydro-Cy7. The mean fluorescent intensity, from the abdominal area, from the three sets of mice was also quantified using Image-Pro software. The results are shown in FIG. 7. LPS-treated mice had approximately two-fold higher fluorescence intensity than the saline group. Taken together, these results indicate the hydrocyanines can image ROS in vivo.

Example 8

Carotid Artery Ligation Causes an Increase in Superoxide Production and Neointima Formation Mice were anesthetized with ketamine/xylazine and their left carotid arteries were exposed and tied with a 6-0 silk suture 1 cm below the bifurcation as described in the literature. The control was sham operated mice. The mice were sacrificed 14 days after ligation and their carotid arteries were isolated and frozen, enzymatically-intact, and 30 µm-thick sections of sham operated and injured carotid arteries were made. The frozen sections were incuvated with DHE (10 µmol/L) in PBS for 30 minutes at 37° C. in a humidified chamber protected form light. DHE is oxidized on reaction with superoxide to ethidium bromide, which binds to DNA in the nucleus and fluoresces red. The DHE stained slides were imaged on a confocal microscope. The ethidium bromide fluorescence was detected using a 543 nm He—Ne laser for excitation and a 560 nm long pass filter for emission. The autofluorescence of the elastic laminae was detected using a 488 nm Ar laser for excitation combined with a 500-550 nm band pass filter for emission. ROS production increased dramatically during carotid ligation as evidenced by increased red fluorescence compared to the sham mice. Histological analysis revealed that carotid ligation generates intense neointima formation, which is a hallmark of atherosclerotic diseases, and that neointima formation correlates with increased ROS production.

Unless defined otherwise, all technical and scientific Winos used herein have the same meanings as commonly understood by one of skill in the art to which the disclosed invention belongs.

We claim:

1. A method of detecting reactive oxygen species, the method comprising contacting cells, cell cultures, tissues, organs, biological fluids, or combinations thereof, with an effective amount of one or more reduced dyes selected from the group consisting of hydrocyanines, deuterocyanines, and combinations thereof and determining if the reduced dye has been oxidized.

2. The method of claim 1, wherein oxidation of the reduced dye is detected by fluorescence spectroscopy.

3. The method of claim 1, wherein the oxidation of the reduced dye is detected by fluorescence microscopy.

4. The method of claim 3, wherein the oxidation of the reduced dye is detected by confocal laser scanning microscopy.

5. The method of claim 3, wherein the oxidation of the reduced dye is detected by total internal reflection fluorescence microscopy.

6. The method of claim 1, wherein the reduced dye is a hydrocyanine.

7. The method of claim 6, wherein the reduced dye is a deuterocyanine.

8. The method of claim 1, wherein the hydrocyanine or deuterocyanine is selected from the group consisting of:

a)

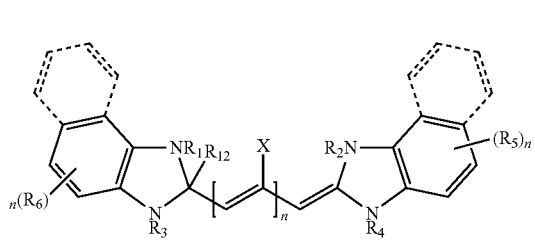

wherein X is hydrogen; halogen; $C_{1-20}$ alkyl; aryl; —OR, where R is $C_{1-20}$ alkyl or aryl; hydroxyl; —$NR_5R_6$, where $R_5$ and $R_6$ are independently hydrogen, $C_{1-20}$ alkyl or aryl; —CN, —SH; —$NO_2$; —S—$C_{1-20}$ alkyl; —S-aryl; aryl, —COOH; —COH; —COR or —COOR, where R is defined above; or —$CONR_{13}R_{14}$, wherein $R_{13}$ and $R_{14}$ are independently hydrogen or R as defined above;

$R_1$-$R_4$ are independently hydrogen, $C_{1-20}$ alkyl, $C_{1-20}$ alkyl sulfate, $C_{1-20}$ alkyl carboxylate; $C_{1-20}$ alkyl amino; aryl, benzyl, oligoethylene glycol, or polyethylene glycol;

$R_5$ and $R_6$ are independently hydrogen; hydroxyl; —$OR_8$; —$NH_2$; —$NHR_9$; —$NR_{10}R_{11}$, $C_{1-20}$ alkyl, $C_{1-20}$ alkyl sulfonate, $C_{1-20}$ alkyl carboxylic acid or carboxylate; $C_{1-20}$ alkyl amino or quaternized amino; —COOH; —$CO_2^-$ or —$SO_3^-$; wherein $R_8$-$R_{11}$ are the same as R; oligoethylene glycol, or polyethylene glycol;

n is an integer from 1-5;

$R_{12}$ is H or D; and the benzene ring represented by dotted lines is optional;

(b)

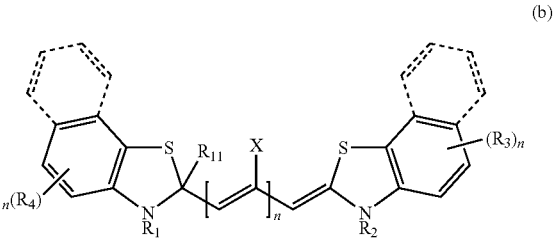

wherein X is hydrogen; halogen; $C_{1-20}$ alkyl; aryl; —OR, where R is $C_{1-20}$ alkyl or aryl; hydroxyl; —$NR_5R_6$, where $R_5$ and $R_6$ are independently hydrogen, $C_{1-20}$ alkyl or aryl; —CN, —SH; —$NO_2$; —S—$C_{1-20}$ alkyl; —S-aryl; aryl, —COOH; —COH; —COR or —COOR, where R is defined above; or —CONR$_{12}$R$_{13}$, wherein R$_{12}$ and R$_{13}$ are independently hydrogen or R as defined above;

R$_1$ and R$_2$ are independently hydrogen, C$_{1-20}$ alkyl, C$_{1-20}$ alkyl sulfonate, C$_{1-20}$ alkyl carboxylic acid or carboxylate; C$_{1-20}$ alkyl amino or quaternized amino; aryl, benzyl, oligoethylene glycol, or polyethylene glycol;

R$_3$ and R$_4$ are independently hydrogen; hydroxyl; —OR$_7$; —NH$_2$; —NHR$_8$; —NR$_9$R$_{10}$, C$_{1-20}$ alkyl, C$_{1-20}$ alkyl sulfate, C$_{1-20}$ alkyl carboxylate; C$_{1-20}$ alkyl amino; —COOH; —CO$_2$$^-$ or —SO$_3$$^-$; wherein R$_7$-R$_{10}$ are the same as R; oligoethylene glycol, or polyethylene glycol;

n is an integer from 1-5;

R$_{11}$ is H or D, and the benzene ring represented by dotted lines is optional;

(c)

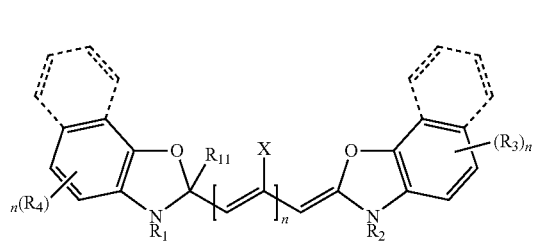

wherein X is hydrogen; halogen; C$_{1-20}$ alkyl; aryl; —OR, where R is C$_{1-20}$ alkyl or aryl; hydroxyl; —NR$_5$R$_6$, where R$_5$ and R$_6$ are independently hydrogen, C$_{1-20}$ alkyl or aryl; —CN, —SH; —NO$_2$; —S—C$_{1-20}$ alkyl; —S-aryl; aryl, —COOH; —COH;

—COR or

—COOR, where R is defined above; or —CONR$_{12}$R$_{13}$, wherein R$_{12}$ and R$_{13}$ are independently hydrogen or R as defined above;

R$_1$ and R$_2$ are independently hydrogen, C$_{1-20}$ alkyl, C$_{1-20}$ alkyl sulfonate, C$_{1-20}$ alkyl carboxylic acid or carboxylate; C$_{1-20}$ alkyl amino or quaternized amino; aryl, benzyl, oligoethylene glycol, or polyethylene glycol;

R$_3$ and R$_4$ are independently hydrogen; hydroxyl; —OR$_7$; —NH$_2$; —NHR$_8$; —NR$_9$R$_{10}$, C$_{1-20}$ alkyl, C$_{1-20}$ alkyl sulfate, C$_{1-20}$ alkyl carboxylate; C$_{1-20}$ alkyl amino; —COOH; —CO$_2$$^-$ or —SO$_3$$^-$; wherein R$_7$-R$_{10}$ are the same as R; oligoethylene glycol, or polyethylene glycol;

n is an integer from 1-5;

R$_{11}$ is H or D; and the benzene ring represented by dotted lines is optional (d)

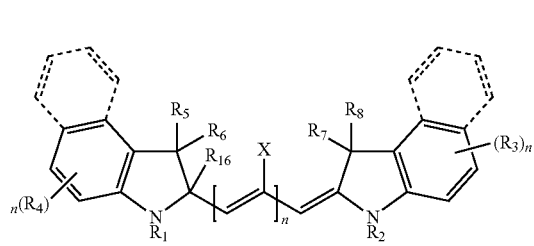

wherein X is hydrogen; halogen; C$_{1-20}$ alkyl; aryl; —OR, where R is C$_{1-20}$ alkyl or aryl; hydroxyl; —NR$_5$R$_6$, where R$_5$ and R$_6$ are independently hydrogen, C$_{1-20}$ alkyl or aryl; —CN, —SH; —NO$_2$, —S—C$_{1-20}$ alkyl; —S-aryl; aryl, —COOH;

—COH; —COR or

—COOR, where R is defined above; or —CONR$_{17}$R$_{18}$, wherein R$_{17}$ and R$_{18}$ are independently hydrogen or R as defined above;

R$_1$ and R$_2$ are independently hydrogen, C$_{1-20}$ alkyl, C$_{1-20}$ alkyl sulfonate, C$_{1-20}$ alkyl carboxylic acid or carboxylate; C$_{1-20}$ alkyl amino or quaternized amino; aryl, benzyl, oligoethylene glycol, or polyethylene glycol;

R$_3$ and R$_4$ are independently hydrogen; hydroxyl; —OR$_{12}$; —NHR$_{13}$;

—NR$_{14}$R$_{15}$, C$_{1-20}$ alkyl, C$_{1-20}$ alkyl sulfate, C$_{1-20}$ alkyl carboxylate; C$_{1-20}$ alkyl amino; —COOH; —CO$_2$$^-$ or —SO$_3$$^-$; wherein R$_{12}$-R$_{15}$ are the same as R; oligoethylene glycol, or polyethylene glycol;

R$_5$-R$_8$ are independently hydrogen or C$_{1-20}$ alkyl;

n is an integer from 1-5;

R$_{16}$ is H or D; and the benzene ring represented by dotted lines is optional, wherein if the benzene ring is not present, R$_{16}$ is D;

(e)

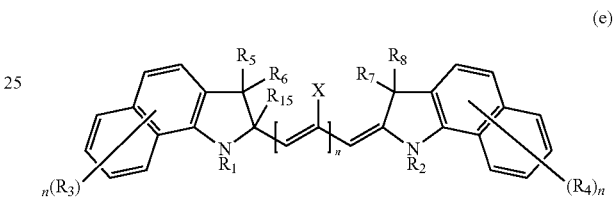

wherein X is hydrogen; halogen; C$_{1-20}$ alkyl; aryl; —OR, where R is C$_{1-20}$ alkyl or aryl; hydroxyl; —NR$_5$R$_6$, where R$_5$ and R$_6$ are independently hydrogen, C$_{1-20}$ alkyl or aryl; —CN, —SH; —NO$_2$, —S—C$_{1-20}$ alkyl; —S-aryl; aryl, —COOH;

—COH; —COR or —COOR, where R is defined above; or —CONR$_{16}$R$_{17}$, wherein R$_{16}$ and R$_{17}$ are independently hydrogen or R as defined above;

R$_1$ and R$_2$ are independently hydrogen, C$_{1-20}$ alkyl, C$_{1-20}$ alkyl sulfonate, C$_{1-20}$ alkyl carboxylic acid or carboxylate; C$_{1-20}$ alkyl amino or quaternized amino; aryl, benzyl, oligoethylene glycol, or polyethylene glycol;

R$_3$ and R$_4$ are independently hydrogen; hydroxyl; —OR$_{11}$; —NHR$_{12}$;

—NR$_{13}$R$_{14}$, C$_{1-20}$ alkyl, C$_{1-20}$ alkyl sulfate, C$_{1-20}$ alkyl carboxylate; C$_{1-20}$ alkyl amino; —COOH; —CO$_2$$^-$ or —SO$_3$$^-$; wherein R$_{11}$-R$_{14}$ are the same as R; oligoethylene glycol, or polyethylene glycol;

R$_5$-R$_8$ are independently hydrogen or C$_{1-20}$ alkyl;

R$_{15}$ is H or D; and n is an integer from 1-5;

(f)

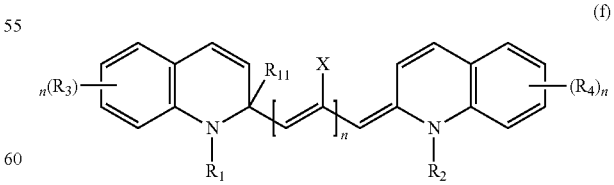

wherein X is hydrogen; halogen; C$_{1-20}$ alkyl; aryl; —OR, where R is C$_{1-20}$ alkyl or aryl; hydroxyl; —NR$_5$R$_6$, where R$_5$ and R$_6$ are independently hydrogen, C$_{1-20}$ alkyl or aryl; —CN, —SH; —NO$_2$; —S—C$_{1-20}$ alkyl; —S-aryl; aryl, —COOH;

—COH; —COR or —COOR, where R is defined above; or —CONR$_{12}$R$_{13}$, wherein R$_{12}$ and R$_{13}$ are independently hydrogen or R as defined above;

R$_1$ and R$_2$ are independently hydrogen, C$_{1-20}$ alkyl, C$_{1-20}$ alkyl sulfonate, C$_{1-20}$ alkyl carboxylic acid or carboxylate; C$_{1-20}$ alkyl amino or quaternized amino; aryl, benzyl, oligoethylene glycol, or polyethylene glycol;

R$_3$ and R$_4$ are independently hydrogen; hydroxyl; —OR$_7$; —NHR$_8$;

—NR$_9$R$_{10}$, C$_{1-20}$ alkyl, C$_{1-20}$ alkyl sulfate, C$_{1-20}$ alkyl carboxylate; C$_{1-20}$ alkyl amino; oligoethylene glycol, or polyethylene glycol;

—COOH; —CO$_2^-$ or —SO$_3^-$; wherein R$_7$-R$_{10}$ are the same as R;

R$_{11}$ is H or D; and n is an integer from 1-5;

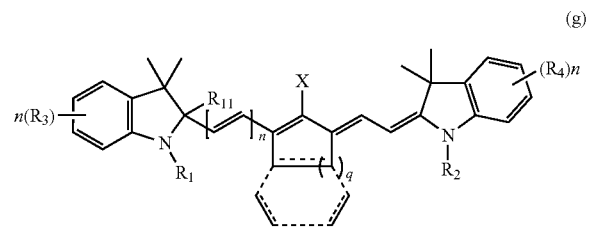

(g)

wherein X is hydrogen; halogen; C$_{1-20}$ alkyl; aryl; —OR, where R is C$_{1-20}$ alkyl or aryl; hydroxyl; —NR$_5$R$_6$, where R$_5$ and R$_6$ are independently hydrogen, C$_{1-20}$ alkyl or aryl; —CN, —SH; —NO$_2$; —S—C$_{1-20}$ alkyl; —S-aryl; aryl, —COOH; —COH; —COR or —COOR, where R is defined above; or —CONR$_{12}$R$_{13}$, wherein R$_{12}$ and R$_{13}$ are independently hydrogen or R as defined above;

R$_1$ and R$_2$ are independently hydrogen, C$_{1-20}$ alkyl, C$_{1-20}$ alkyl sulfonate, C$_{1-20}$ alkyl carboxylic acid or carboxylate; C$_{1-20}$ alkyl amino or quaternized amino; aryl, benzyl, oligoethylene glycol, or polyethylene glycol; and R$_3$ and R$_4$ are independently hydrogen; hydroxyl; —OR$_7$; —NHR$_8$;

—NR$_9$R$_{10}$, C$_{1-20}$ alkyl, C$_{1-20}$ alkyl sulfate, C$_{1-20}$ alkyl carboxylate; C$_{1-20}$ alkyl amino; —COOH; —CO$_2^-$ or —SO$_3^-$; wherein R$_7$-R$_{10}$ are the same as R; oligoethylene glycol, or polyethylene glycol;

n is an integer from 1-5; and q is 0, 1, or 2;

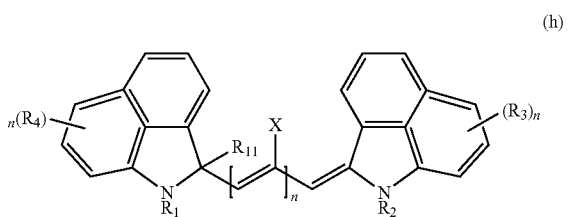

(h)

wherein X is hydrogen; halogen; C$_{1-20}$ alkyl; aryl; —OR, where R is C$_{1-20}$ alkyl or aryl; hydroxyl; —NR$_5$R$_6$, where R$_5$ and R$_6$ are independently hydrogen, C$_{1-20}$ alkyl or aryl; —CN, —SH; —NO$_2$; —S—C$_{1-20}$ alkyl; —S-aryl; aryl, —COOH; —COH; —COR or —COOR, where R is defined above; or —CONR$_{12}$R$_{13}$, wherein R$_{12}$ and R$_{13}$ are independently hydrogen or R as defined above;

R$_1$ and R$_2$ are independently hydrogen, C$_{1-20}$ alkyl, C$_{1-20}$ alkyl sulfonate, C$_{1-20}$ alkyl carboxylic acid or carboxylate; C$_{1-20}$ alkyl amino or quaternized amino; aryl, benzyl, oligoethylene glycol, or polyethylene glycol; and R$_3$ and R$_4$ are independently hydrogen; hydroxyl; —OR$_7$; —NHR$_8$;

—NR$_9$R$_{10}$, C$_{1-20}$ alkyl, C$_{1-20}$ alkyl sulfate, C$_{1-20}$ alkyl carboxylate; C$_{1-20}$ alkyl amino; —COOH; —CO$_2^-$ or —SO$_3^-$;

wherein R$_7$-R$_{10}$ are the same as R; oligoethylene glycol, or polyethylene glycol;

R$_{11}$ is D; and n is an integer from 1-5;

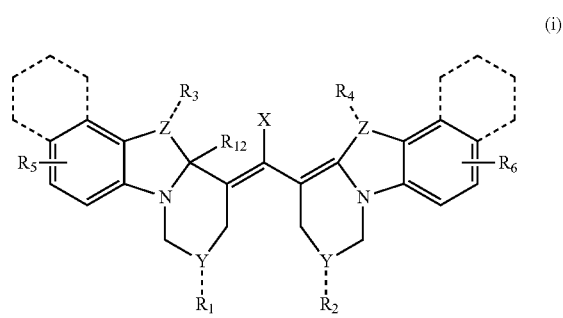

(i)

wherein X is hydrogen; halogen; C$_{1-20}$ alkyl; aryl; —OR, where R is C$_{1-20}$ alkyl or aryl; hydroxyl; —NR$_5$R$_6$, where R$_5$ and R$_6$ are independently hydrogen, C$_{1-20}$ alkyl or aryl; —CN, —SH; —NO$_2$; —S—C$_{1-20}$ alkyl; —S-aryl; aryl, —COOH;

—COH; —COR or —COOR, where R is defined above; or —CONR$_{13}$R$_{14}$, wherein R$_{13}$ and R$_{14}$ are independently hydrogen or R as defined above;

R$_1$-R$_4$ are independently hydrogen, C$_{1-20}$ alkyl; C$_{1-20}$ alkyl sulfonate, C$_{1-20}$ alkyl carboxylic acid or carboxylate; C$_{1-20}$ alkyl amino or quaternized amino; aryl, benzyl, oligoethylene glycol, or polyethylene glycol;

R$_5$ and R$_6$ are independently hydrogen; hydroxyl; —OR$_5$; —NH$_2$; —NHR$_6$; —NR$_7$R$_8$, C$_{1-20}$ alkyl; C$_{1-20}$ alkyl sulfate; C$_{1-20}$ alkyl carboxylate; C$_{1-20}$ alkyl amino; —COOH; —CO$_2^-$; or —SO$_3^-$; wherein R$_5$-R$_8$ are the same as R; oligoethylene glycol, or polyethylene glycol;

Y and Z are independently carbon, nitrogen or sulfur, wherein if Y and/or Z is carbon, the carbon is tetravalent having two substituents as defined above; if Y and/or Z is sulfur; the sulfur is divalent; and if Y and/or Z is nitrogen, the nitrogen is trivalent, having one substituent as defined above;

R$_{12}$ is H or D; and the benzene ring represented by dotted lines is optional;

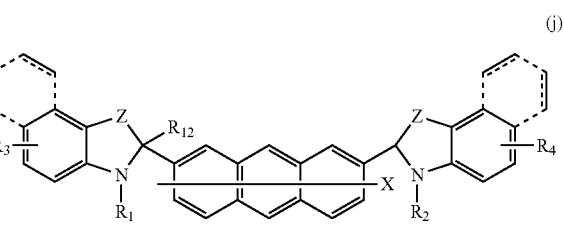

(j)

wherein X is hydrogen; halogen; C$_{1-20}$ alkyl; aryl; —OR, where R is C$_{1-20}$ alkyl or aryl; hydroxyl; —NR$_5$R$_6$, where R$_5$ and R$_6$ are independently hydrogen, C$_{1-20}$ alkyl or aryl; —CN, —SH; —NO$_2$; —S—C$_{1-20}$ alkyl; —S-aryl; —COOH; —COH; —COR or —COOR, where R is defined above; or —CONR$_{13}$R$_{14}$, wherein R$_{13}$ and R$_{14}$ are independently hydrogen or R as defined above;

- R$_1$ and R$_2$ are independently hydrogen, C$_{1-20}$ alkyl; C$_{1-20}$ alkyl sulfonate, C$_{1-20}$ alkyl carboxylic acid or carboxylate; C$_{1-20}$ alkyl amino or quaternized amino; aryl, benzyl, oligoethylene glycol, or polyethylene glycol;
- R$_3$ and R$_4$ are independently hydrogen; hydroxyl; —OR$_5$; —NH$_2$; —NHR$_6$; —NR$_7$R$_8$, C$_{1-20}$ alkyl; C$_{1-20}$ alkyl sulfonate, C$_{1-20}$ alkyl carboxylic acid or carboxylate; C$_{1-20}$ alkyl amino or quaternized amino; —COOH; —CO$_2^-$; or —SO$_3^-$; wherein R$_5$-R$_8$ are independent selected from the group consisting of C$_{1-20}$ alkyl or aryl; oligoethylene glycol, or polyethylene glycol;
- Z is carbon, nitrogen, sulfur, or oxygen, wherein if Y and/or Z is carbon, the carbon is tetravalent having two substituents as defined above; if Y and/or Z is sulfur and/or oxygen; the sulfur and/or oxygen is divalent; and if Y and/or Z is nitrogen, the nitrogen is trivalent, having one substituent as defined above;
- R$_{12}$ is H or D; and the benzene ring represented by dotted lines is optional.

9. The method of claim 8, wherein the hydrocyanine or deuterocyanine is a compound of formula (d).

10. The method of claim 9, wherein the benzene ring is absent.

11. The method of claim 10, wherein X=H, R$_1$ and R$_2$=methyl, ethyl, or (CH$_2$)$_4$SO$_3$Na, R$_3$ and R$_4$=H, R$_5$-R$_8$=methyl, and R$_{16}$=D or H.

12. The method of claim 9, wherein the benzene ring is present.

13. The method of claim 12, wherein X=H, R$_1$ and R$_2$=methyl, ethyl, or (CH$_2$)$_4$SO$_3$Na, R$_3$ and R$_4$=H, R$_5$-R$_8$=methyl, and R$_{16}$=D or H.

14. The method of claim 8, wherein the hydrocyanine or deuterocyanine is a compound of formula (g).

15. The method of claim 14, wherein X=Cl, q=2, n=1, R$_3$ and R$_4$=H, R$_1$ and R$_2$=(CH$_2$)$_4$SO$_3$Na, and R$_{11}$ is hydrogen or deuterium.

16. The method of claim 1, wherein the cells, tissue, biological fluids, or combinations thereof are contacted with the one or more reduced dyes in vitro.

17. The method of claim 1, wherein the cells, tissue, biological fluids, or combinations thereof are contacted with the one or more reduced dyes in vivo.

* * * * *